(12) United States Patent
Kamee et al.

(10) Patent No.: US 11,910,106 B2
(45) Date of Patent: Feb. 20, 2024

(54) LIGHT SOURCE DEVICE AND ENDOSCOPE SYSTEM INCLUDING THE SAME

(71) Applicant: OLYMPUS CORPORATION, Tokyo (JP)

(72) Inventors: Hiroyuki Kamee, Koganei (JP); Takeshi Ito, Hino (JP); Masahiro Nishio, Hachioji (JP); Satoshi Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 18/358,187

(22) Filed: Jul. 25, 2023

(65) Prior Publication Data

US 2023/0370732 A1   Nov. 16, 2023

Related U.S. Application Data

(63) Continuation of application No. PCT/JP2021/033798, filed on Sep. 14, 2021.

(51) Int. Cl.

| | |
|---|---|
| *H04N 25/11* | (2023.01) |
| *H04N 23/10* | (2023.01) |
| *H04N 23/56* | (2023.01) |
| *H04N 23/50* | (2023.01) |
| *H04N 23/55* | (2023.01) |
| *G02B 23/24* | (2006.01) |

(52) U.S. Cl.
CPC ......... *H04N 25/11* (2023.01); *G02B 23/2461* (2013.01); *H04N 23/10* (2023.01); *H04N 23/55* (2023.01); *H04N 23/555* (2023.01); *H04N 23/56* (2023.01)

(58) Field of Classification Search
CPC ........ H04N 25/11; H04N 23/10; H04N 23/55; H04N 23/555; H04N 23/56; G02B 23/2461; A61B 1/07; H05B 45/22
See application file for complete search history.

(56) References Cited

U.S. PATENT DOCUMENTS

| | | | |
|---|---|---|---|
| 7,847,785 B2 | 12/2010 | Tanaka | |
| 10,045,431 B2 * | 8/2018 | Otani | ..................... H04N 23/74 |
| 10,610,091 B2 * | 4/2020 | Onobori | ............... A61B 1/0676 |
| 2009/0017431 A1 | 1/2009 | Adams | |

FOREIGN PATENT DOCUMENTS

| | | |
|---|---|---|
| JP | 2008282936 A | 11/2008 |
| JP | 2009129687 A | 6/2009 |
| JP | 2017099944 A | 6/2017 |
| JP | 2018198189 A | 12/2018 |
| WO | 2009031103 A1 | 3/2009 |

OTHER PUBLICATIONS

International Search Report dated Dec. 14, 2021 issued in PCT/JP2021/033798.

* cited by examiner

*Primary Examiner* — Seung C Sohn

(74) *Attorney, Agent, or Firm* — Scully, Scott, Murphy & Presser, P.C.

(57) ABSTRACT

A light source device includes a plurality of light emitters, an optical system configured to combine light from the light emitters, a wavelength selective filter located on an optical path of the optical system, and an optical sensor configured to receive light from one light emitter among the light emitters through an optical filter. The optical filter has a wavelength selection characteristic corresponding to a wavelength selection characteristic of the wavelength selective filter.

8 Claims, 13 Drawing Sheets

LIGHT SOURCE DEVICE AND ENDOSCOPE SYSTEM INCLUDING THE SAME

CROSS-REFERENCE TO RELATED APPLICATION

The present application is a continuation application of PCT/JP2021/033798 filed on Sep. 14, 2021; the entire contents of which are incorporated herein by reference.

BACKGROUND

Technical Field

The present disclosure relates to a light source device and an endoscope system including the same.

Description of the Related Art

A light source device is disclosed in Japanese Unexamined Patent Application Publication No. 2017-099944. In this light source device, illumination light suitable for normal observation and illumination light suitable for vascular enhancement observation are generated.

The light source device includes four light emitters. Illumination light suitable for normal observation can be obtained using three light emitters. Illumination light suitable for vascular enhancement observation can be obtained using four light emitters.

It is possible to express the color balance in illumination light using the light quantity in each of the light emitters. In illumination in normal observation, three light emitters are used. Therefore, the color balance in illumination light for normal observation is expressed in the ratio of three light quantities. In illumination in vascular enhancement observation, four light emitters are used. Therefore, the color balance in illumination light for vascular enhancement observation is expressed in the ratio of four light quantities.

The color balance in illumination light most suitable for observation is referred to as ideal color balance. The ratio of light quantity in the ideal color balance represents the ideal ratio of light quantity.

In a light emitter, the light quantity may change with temperature. When the light quantity changes, the ratio of light quantity changes. For this reason, the color balance in illumination light is disturbed. In the illumination light with the color balance disturbed, the ratio of light quantity does not match the ideal ratio of light quantity. As a result, it is impossible to maintain the ideal color balance.

In illumination light for normal observation, the ratio of three light quantities does not match the ideal ratio of light quantity when the light quantity changes. In illumination light for vascular enhancement observation, the ratio of four light quantities does not match the ideal ratio of light quantity when the light quantity changes. In both cases, it is impossible to maintain the ideal color balance. For this reason, it is difficult to obtain illumination light suitable for observation.

A dichroic mirror is used in the light source device. Light emitted from the light emitter is incident on the dichroic mirror. Predetermined light is emitted from the dichroic mirror. The predetermined light is light having exactly the same wavelength band as the wavelength band of the light emitted from the light emitter. The predetermined light may be light having substantially the same wavelength band as the wavelength band of the light emitted from the light emitter.

In normal observation and vascular enhancement observation, the predetermined light is used as illumination light. When the light quantity in the light emitter changes, the light quantity of the predetermined light changes. As a result, the color balance in the illumination light is disturbed.

In the light source device, a light-receiving unit is provided for each of the light emitters. The light emitted from the light emitter is incident on the light-receiving unit. When the light having exactly the same wavelength band as the wavelength band of the light emitted from the light emitter is the predetermined light, it is possible to consider the predetermined light as being detected by the light-receiving unit.

Adjustment of the light quantity in the light emitter is performed based on the light detected by the light-receiving unit. It is possible to consider the light detected by the light-receiving unit as the predetermined light. Thus, when the light quantity in the light emitter changes, it is possible to maintain the ideal color balance by performing adjustment. As a result, illumination light suitable for observation can be obtained.

As described above, the light incident on the light-receiving unit is the light emitted from the light emitter. When the light having substantially the same wavelength band as the wavelength band of the light emitted from the light emitter is the predetermined light, the predetermined light is slightly different from the light emitted from the light emitter. In this case, it is impossible to consider the predetermined light as being detected by the light-receiving unit.

In the light source device, a wavelength-limiting filter is used in two light-receiving units. The wavelength band of light emitted from the wavelength-limiting filter is identical to the wavelength band of light emitted from the dichroic mirror. Therefore, it is possible to consider the predetermined light as being detected by the light-receiving unit.

Special light observation, for example, narrow-band light observation, is known as an observation technique. Illumination light for narrow-band light observation includes light in a partial wavelength band (hereinafter referred to as "partial band light") of the wavelength band of the light emitted from the light emitter.

SUMMARY

A light source device according to at least some embodiments of the present disclosure includes:
 a plurality of light emitters;
 an optical system configured to combine light from the light emitters;
 a wavelength selective filter located on an optical path of the optical system; and
 an optical sensor configured to receive light from one light emitter among the light emitters through an optical filter, wherein
 the optical filter has a wavelength selection characteristic corresponding to a wavelength selection characteristic of the wavelength selective filter.

An endoscope system according to at least some embodiments of the present disclosure includes:
 an endoscope;
 a video processor;
 a monitor; and
 the light source device described above.

DETAILED DESCRIPTION

For a light source device of the present embodiment and an endoscope system of the present embodiment, the reason and action of these configurations will be described below with reference to the drawings. The present disclosure is not limited by the following embodiments.

In a description of the embodiments, a wavelength selective filter, an optical filter, and a dichroic mirror are used. In these optical elements, light transmission and light reflection occur depending on the wavelength. As a result, it is possible to select light of a specific wavelength or light of a specific wavelength band in these optical elements.

The characteristic of selecting light of a specific wavelength or a specific wavelength band from incident light and effectively using the selected light as illumination light or the like is referred to as wavelength selection characteristic. The wavelength selection characteristic can be expressed in transmittance or reflectance, because it is possible to effectively use the transmitted light of a desired wavelength or effectively use the reflected light of a desired wavelength, depending on the configuration of an optical system. The wavelength selection characteristic can be rephrased as transmission characteristic, reflection characteristic, or transmission/reflection characteristic.

The light source device of the present embodiment includes a plurality of light emitters. It is possible to use light emitted from the light emitter for illumination of an object. Hereinafter "illumination light" is used in description.

The light emitted from the light emitter ultimately irradiates an object. In the light source device of the present embodiment, for example, a dichroic mirror is used. Thus, the wavelength band of the light emitted from the light emitter may differ from the wavelength band of the light irradiating an object. The "illumination light" described above means the light emitted from the light emitter and does not mean the light irradiating an object.

The light source device of the present embodiment includes a plurality of light emitters, an optical system configured to combine light from the light emitters, a wavelength selective filter located on an optical path of the optical system, and an optical sensor configured to receive light from one light emitter among the light emitters through an optical filter. The optical filter has a wavelength selection characteristic corresponding to a wavelength selection characteristic of the wavelength selective filter.

Figure 1A:
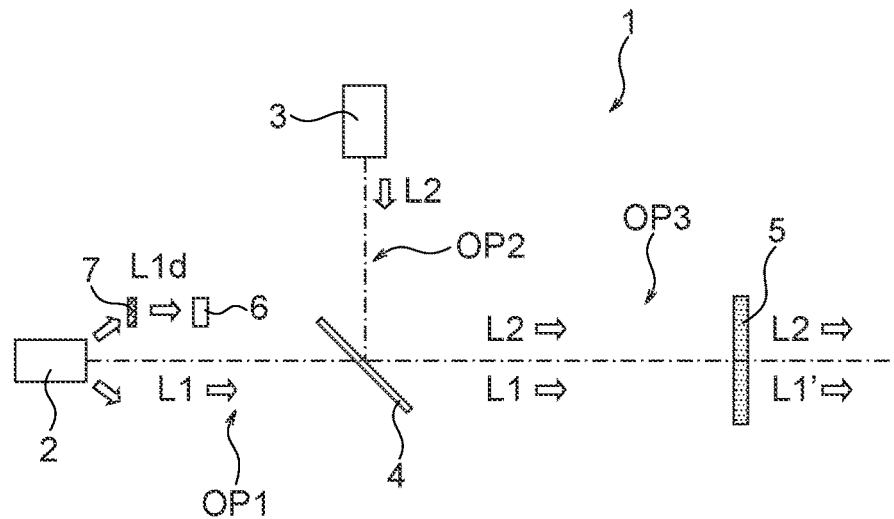
FIGS. 1A, 1B, and 1C are diagrams illustrating a light source device of the present embodiment, the wavelength band of illumination light, and the wavelength selection characteristic of a wavelength selective filter.
Figure 1B:
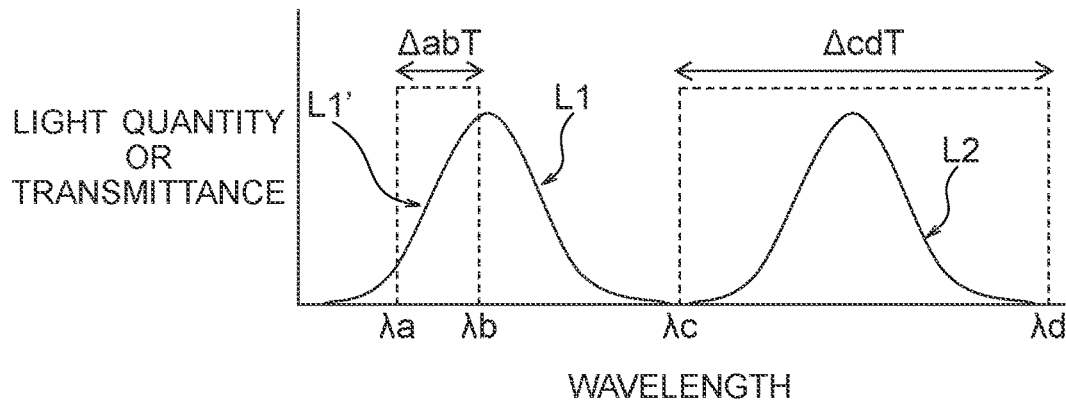
Figure 1C:
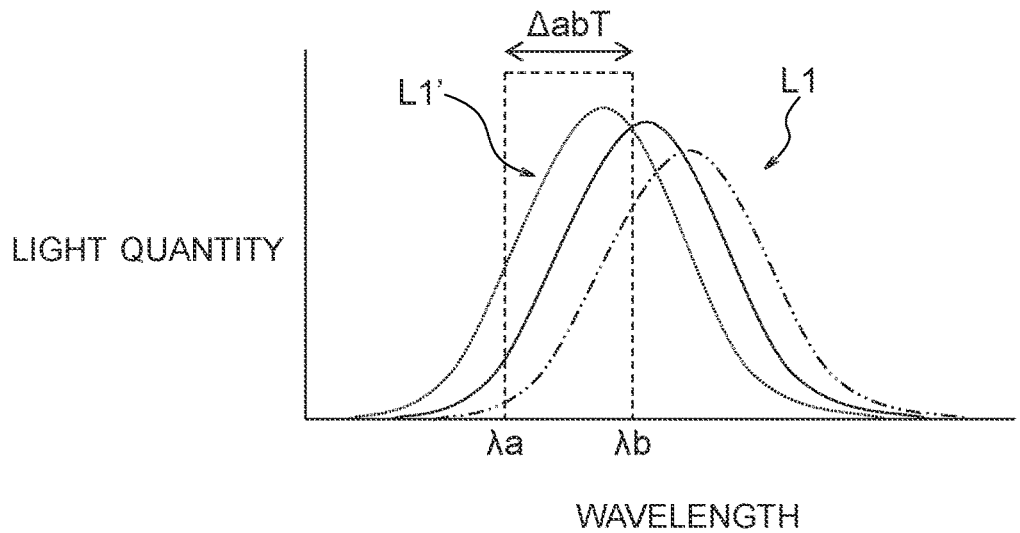

FIGS. 1A, 1B, and 1C are diagrams illustrating a light source device of the present embodiment, the wavelength band of illumination light, and the wavelength selection characteristic of a wavelength selective filter.

FIG. 1A is a diagram illustrating a first example of the light source device of the present embodiment. FIG. 1B is a diagram illustrating the wavelength band of illumination light and the wavelength selection characteristic of a wavelength selective filter. FIG. 1C is a diagram illustrating change in light quantity in illumination light and the wavelength selection characteristic of a wavelength selective filter.

The light source device of the first example will be described. The light source device of the first example includes a plurality of light emitters. In the light source device of the first example, two light emitters are used. The light quantity in one of the light emitters changes with temperature, and the light quantity in the other light emitter does not change with temperature.

As illustrated in FIG. 1A, a light source device 1 includes a light emitter 2 and a light emitter 3. In the light emitter 2, the light quantity changes with temperature. In the light emitter 3, the light quantity does not change with temperature.

The light source device 1 further includes a dichroic mirror 4, a wavelength selective filter 5, an optical sensor 6, and an optical filter 7.

Illumination light L1 is emitted from the light emitter 2. The illumination light L1 travels through a first optical path OP1. Illumination light L2 is emitted from the light emitter 3. The illumination light L2 travels through a second optical path OP2.

The dichroic mirror 4 is disposed at the position where the first optical path OP1 and the second optical path OP2 intersect. The illumination light L1 and the illumination light L2 are incident on the dichroic mirror 4.

In FIG. 1B, the wavelength band of the illumination light L1 and the wavelength band of the illumination light L2 are depicted by solid lines. Further, the wavelength selection characteristic of the wavelength selective filter 5 is depicted by a broken line. The horizontal axis indicates wavelength. The vertical axis indicates light quantity or transmittance.

The wavelength band of the illumination light L1 is located on the shorter wavelength side than the wavelength band of the illumination light L2. The dichroic mirror 4 has a characteristic of transmitting light with short wavelengths and reflecting light with long wavelengths. The illumination light L1 is transmitted through the dichroic mirror 4, and the illumination light L2 is reflected by the dichroic mirror 4.

In the light source device 1, the illumination light L1 and the illumination light L2 are combined by the dichroic mirror 4. As a result, the illumination light L1 and the illumination light L2 are emitted from the dichroic mirror 4, as illustrated in FIG. 1A. It is possible to say that the dichroic mirror 4 is an optical system that combines the illumination light L1 and the illumination light L2.

The illumination light L1 and the illumination light L2 travel through a third optical path OP3. The wavelength selective filter 5 is located on the emission side of the dichroic mirror 4. The illumination light L1 and the illumination light L2 are incident on the wavelength selective filter 5.

As illustrated in FIG. 1B, the wavelength selective filter 5 has a transmission band ΔabT and a transmission band ΔcdT. The wavelength band of the transmission band ΔabT is from a wavelength λa to a wavelength λb. The wavelength band of the transmission band ΔcdT is from a wavelength λc to a wavelength λd. The wavelength selective filter 5 transmits light in the transmission band ΔabT and light in the transmission band ΔcdT.

As described above, the partial band light is light in a partial wavelength band of the wavelength band of the light emitted from the light emitter. Light from the wavelength λa to the wavelength λb is light in a partial wavelength band of the wavelength band of the illumination light L1. The light from the wavelength λa to the wavelength λb is defined as partial band light L1'. The wavelength band of the partial band light L1' is from the wavelength λa to the wavelength λb.

The wavelength band of the partial band light L1' is the same as the transmission band ΔabT. Therefore, the partial band light L1' is emitted from the wavelength selective filter 5. The wavelength band of the illumination light L2 is included in the transmission band ΔcdT. Therefore, the illumination light L2 is emitted from the wavelength selective filter 5. The partial band light L1' and the illumination light L2 travel through the third optical path OP3.

FIG. 1C illustrates change in light quantity in the illumination light L1 when the temperature changes. The dotted line depicts the light quantity when the temperature is higher than room temperature, the solid line depicts the light quantity at room temperature, and the chain double-dashed line depicts the light quantity when the temperature is lower than room temperature. Further, the wavelength selection characteristic of the wavelength selective filter 5 in the wavelength band of the illumination light L1 is depicted by a broken line. The horizontal axis indicates wavelength. The vertical axis indicates light quantity or transmittance.

As illustrated in FIG. 1C, in the light emitter 2, the light quantity of the illumination light L1 decreases as the temperature decreases. Thus, the light quantity in the transmission band ΔabT also decreases as the temperature decreases. The partial band light L1' is the transmitted light in the transmission band ΔabT. Therefore, the light quantity of the partial band light L1' decreases as the temperature decreases. As a result, the color balance in the illumination light is disturbed.

To maintain the ideal color balance, change in light quantity of the partial band light L1' may be detected, and the light quantity of the light emitter 2 may be adjusted based on the detected result.

Detection of the partial band light L1' may be performed by an optical sensor. However, it is difficult to dispose an optical sensor on the emission side of the wavelength selective filter 5. In the light source device 1, the optical sensor 6 and the optical filter 7 are disposed in proximity to the light emitter 2. It is only necessary that the wavelength band of light emitted from the optical filter 7 should correspond to the wavelength band of the partial band light L1'.

The optical sensor 6 receives light from the light emitter 2 through the optical filter 7. The illumination light L1 is emitted from the light emitter 2. The optical sensor 6 is disposed at a position where the illumination light L1 reaches.

The optical filter 7 is adjacent to the optical sensor 6. In FIG. 1A, the optical filter 7 is separated from the optical sensor 6 for the sake of visibility. The optical filter 7 is disposed between the light emitter 2 and the optical sensor 6. The optical filter 7 is a transmissive optical filter.

The optical filter 7 has a wavelength selection characteristic corresponding to the wavelength selection characteristic of the wavelength selective filter 5. The relation between the transmission band of the optical filter 7 and the transmission band ΔabT is, for example, as follows in the wavelength band of the illumination light L1.

(A) The transmission band of the optical filter 7 is identical to the transmission band ΔabT.
(B) The transmission band of the optical filter 7 includes the transmission band ΔabT.
(C) The transmission band of the optical filter 7 is included in the transmission band ΔabT.
(D) The transmission band of the optical filter 7 is shifted with respect to the transmission band ΔabT.

(B), (C), and (D) mean that the transmission band of the optical filter 7 is substantially identical to the transmission band ΔabT. (B), (C), and (D) are different from (A). However, the difference is such a difference that provides an operation effect similar to that of (A). Therefore, it is possible to consider (B), (C), and (D) as being substantially (A).

In this way, in the optical filter 7, it is only necessary that at least a part of the transmission band should overlap with the transmission band ΔabT. A description will be given below taking the case (A) as an example.

Detection light L1d is detected in the optical sensor 6. The detection light L1d is light transmitted through the optical filter 7. Only the illumination light L1 is incident on the optical filter 7. In this case, the wavelength band of the detection light L1d is the same as the transmission band ΔabT. The transmission band ΔabT is the same as the wavelength band of the partial band light L1'. Therefore, the wavelength band of the detection light L1d is the same as the wavelength band of the partial band light L1'.

When the light quantity of the illumination light L1 changes, the light quantity of the detection light L1d and the light quantity of the partial band light L1' change. Therefore, by detecting change in light quantity of the detection light L1d, it is possible to detect change in light quantity of the partial band light L1'. In the light source device 1, it is possible to adjust the light quantity in the light emitter 2 based on a signal output from the optical sensor 6.

In the adjustment, the light quantity of the detection light L1d is used. As described above, the wavelength band of the detection light L1d is the same as the wavelength band of the partial band light L1'. In this case, adjustment is performed for the light emitter 2, using the same light as the light emitted from the wavelength selective filter 5. Thus, when the light quantity in the light emitter 2 changes, it is possible to maintain the ideal color balance by performing adjustment. As a result, illumination light suitable for observation can be obtained.

When the optical filter 7 is not disposed, the light quantity of the illumination light L1 is used in the adjustment. In this case, adjustment is performed for the light emitter 2, using light different from the light emitted from the wavelength selective filter 5. Thus, when the light quantity in the light emitter 2 changes, it is impossible to maintain the ideal color balance even by performing adjustment. As a result, illumination light suitable for observation is unable to be obtained.

Only partial light of the illumination light L1 is incident on the optical sensor 6. In this case, the light quantity of light detected by the optical sensor 6 is different from the light quantity of light emitted from the wavelength selective filter 5. Therefore, adjustment in the light emitter 2 may be performed in consideration of the difference in light quantity between the two types of light.

In the light source device 1, it is possible to use an LED (light emitting diode) as a light emitter. For example, it is possible to use an LED emitting violet light for the light emitter 2 and use an LED emitting blue light for the light emitter 3. In this case, illumination light consists of violet light and blue light in a narrow band. Therefore, illumination light for narrow-band light observation can be obtained.

The wavelength selective filter 5 transmits light in a partial wavelength band of the wavelength band of the illumination light L1 and light in the entire wavelength band of the illumination light L2. However, the wavelength selective filter 5 may transmit light in the entire wavelength band of the illumination light L1 and light in a partial wavelength band of the wavelength band of the illumination light L2. In this case, the optical sensor and the optical filter may be disposed in proximity to the light emitter 3.

In the light source device of the present embodiment, it is preferable that the wavelength selection characteristic of the optical filter be identical to the wavelength selection characteristic of the wavelength selective filter.

In this case, it is possible to adjust the light quantity in the light emitter 2 with high accuracy. As a result, illumination light even more suitable for observation can be obtained.

Figure 2:
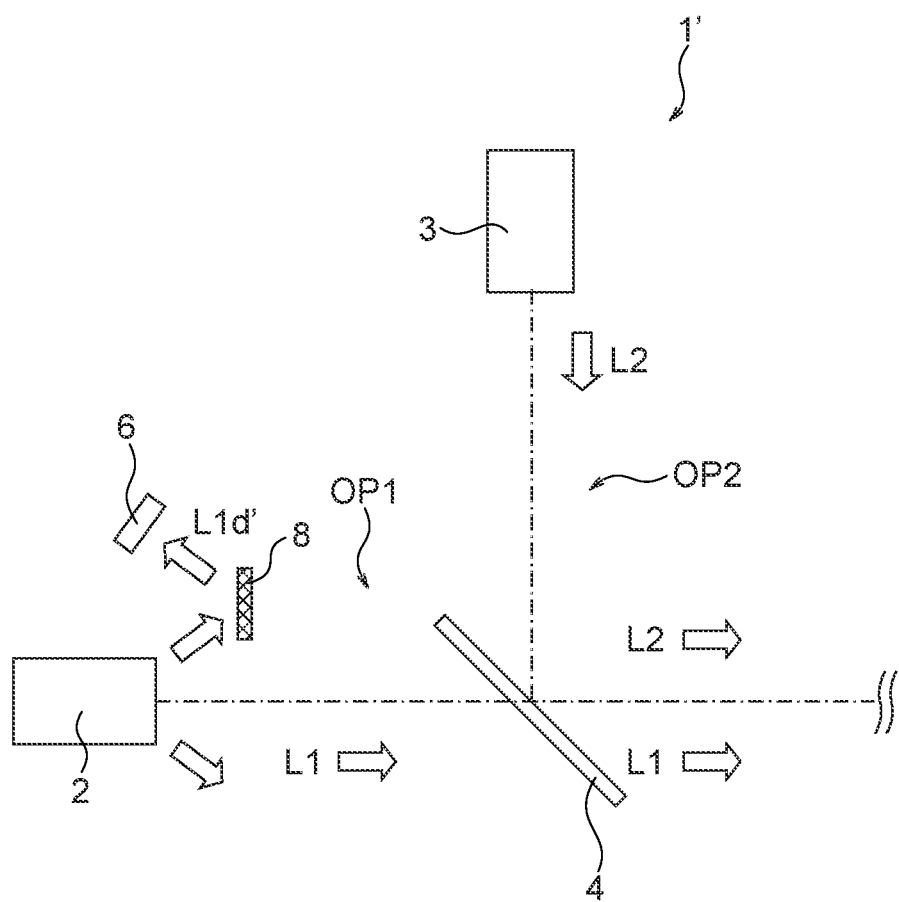
FIG. 2 is a diagram illustrating a first modification of the light source device.

FIG. 2 is a diagram illustrating a first modification of the light source device. The same component as in FIG. 1A is denoted by the same number and a description thereof will be omitted.

A light source device 1' has an optical filter 8. The optical filter 8 is disposed at a position where the illumination light L1 reaches. The optical filter 8 is a reflective optical filter. The optical sensor 6 is disposed at a position away from the optical filter 8.

The optical filter 8 has a wavelength selection characteristic corresponding to the wavelength selection characteristic of the wavelength selective filter 5. The relation between the reflection band of the optical filter 8 and the transmission band ΔabT is similar to the above (A) to (D). It is only necessary to replace the transmission band of the optical filter 7 by the reflection band of the optical filter 8. A description will be given taking the case (A) as an example.

Detection light L1d' is detected in the optical sensor 6. The detection light L1d' is light reflected by the optical filter 8. Only the illumination light L1 is incident on the optical filter 8. In this case, the wavelength band of the detection light L1d' is the same as the transmission band ΔabT. The transmission band ΔabT is the same as the wavelength band of the partial band light L1'. Therefore, the wavelength band of the detection light L1d' is the same as the wavelength band of the partial band light L1'.

When the light quantity of the illumination light L1 changes, the light quantity of the detection light L1d' and the light quantity of the partial band light L1' change. Therefore, by detecting change in light quantity of the detection light L1d', it is possible to detect change in light quantity of the partial band light L1'. In the light source device 1', it is possible to adjust the light quantity in the light emitter 2 based on a signal output from the optical sensor 6.

In the adjustment, the light quantity of the detection light L1d' is used. As described above, the wavelength band of the detection light L1d' is the same as the wavelength band of the partial band light L1'. In this case, adjustment is performed for the light emitter 2, using the same light as the light emitted from the wavelength selective filter 5. Thus, when the light quantity in the light emitter 2 changes, it is possible to maintain the ideal color balance by performing adjustment. As a result, illumination light suitable for observation can be obtained.

It is preferable that the light source device of the present embodiment have a plurality of light emission modes. In the light emission modes, it is preferable that the wavelength band of emitted light be different in each of the light emission modes, and it is preferable that the light emission modes include a first light emission mode in which the wavelength selective filter is located on the optical path and a second light emission mode in which the wavelength selective filter is not located on the optical path.

Figure 3A:
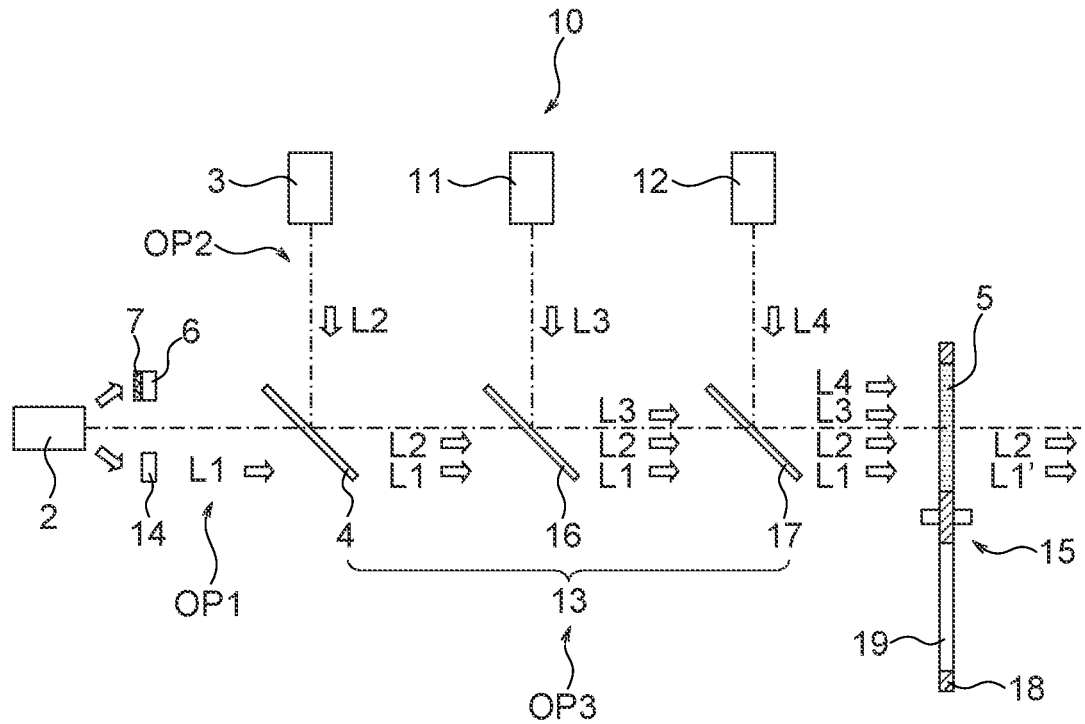
FIGS. 3A and 3B are diagrams illustrating a light source device of the present embodiment.
Figure 3B:
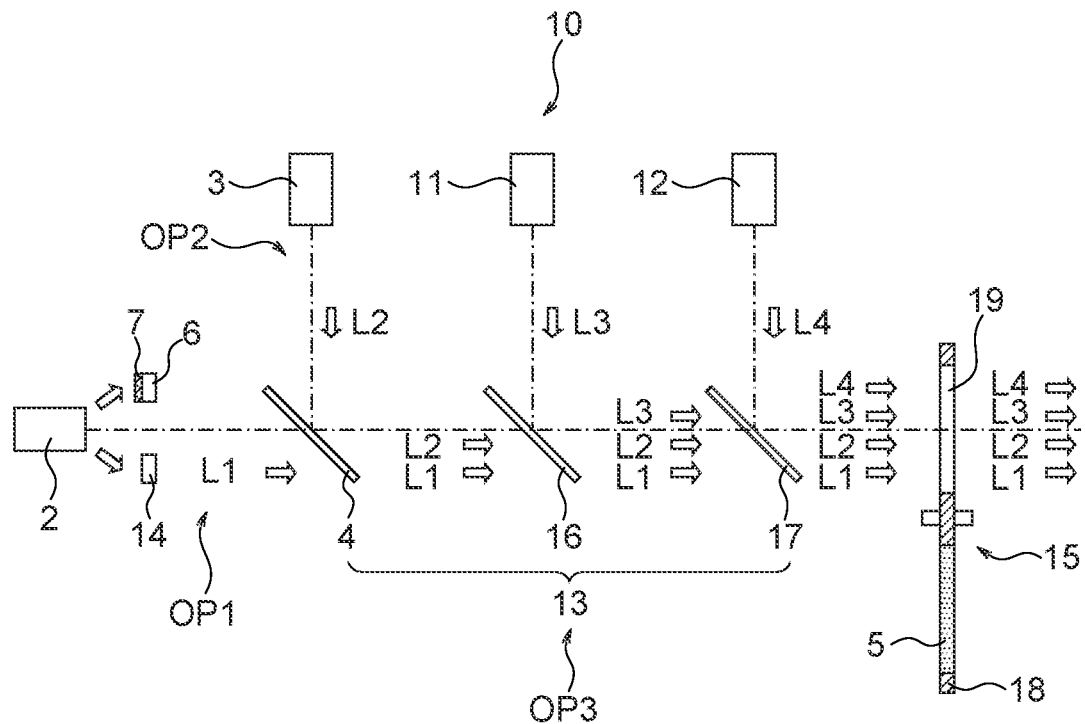

FIGS. 3A and 3B are diagrams illustrating a light source device of the present embodiment. FIGS. 3A and 3B illustrate a second example of the light source device of the present embodiment. FIG. 3A is a diagram illustrating the light source device in a first light emission mode. FIG. 3B is a diagram illustrating the light source device in a second light emission mode. The same component as in FIG. 1A is denoted by the same number and a description thereof will be omitted.

The light source device of the second example will be described. The light source device of the second example includes a plurality of light emitters. In the light source device of the second example, four light emitters are used. The light quantity in one light emitter changes with temperature, and the light quantity in three light emitters does not change with temperature.

As illustrated in FIG. 3A, a light source device 10 includes a light emitter 2, a light emitter 3, a light emitter 11, and a light emitter 12. In the light emitter 2, the light quantity changes with temperature. In the light emitter 3, the light emitter 11, and the light emitter 12, the light quantity does not change with temperature.

The light source device 10 further includes an optical system 13, a wavelength selective filter 5, an optical sensor 6, an optical sensor 14, an optical filter 7, and a rotating member 15.

The optical system 13 includes a dichroic mirror 4, a dichroic mirror 16, and a dichroic mirror 17.

The rotating member 15 includes a rotating plate 18, the wavelength selective filter 5, and a parallel flat plate 19. The wavelength selective filter 5 and the parallel flat plate 19 are held by the rotating plate 18. A colorless, transparent material, such as glass or resin, is used for the parallel flat plate 19.

The parallel flat plate 19 is not necessarily disposed. In this case, the rotating plate 18 includes the wavelength selective filter 5 and a through hole.

Illumination light L3 is emitted from the light emitter 11. The dichroic mirror 16 is disposed on the third optical path OP3. Illumination light L1, illumination light L2, and illumination light L3 are incident on the dichroic mirror 16.

The wavelength band of the illumination light L1 and the wavelength band of the illumination light L2 are located on the shorter wavelength side than the wavelength band of the illumination light L3. The dichroic mirror 16 has a characteristic of transmitting light with short wavelengths and reflecting light with long wavelengths. The illumination light L1 and the illumination light L2 are transmitted through the dichroic mirror 16, and the illumination light L3 is reflected by the dichroic mirror 16.

In the dichroic mirror 16, the illumination light L1, the illumination light L2, and the illumination light L3 are combined. As a result, the illumination light L1, the illumination light L2, and the illumination light L3 are emitted from the dichroic mirror 16.

Illumination light L4 is emitted from the light emitter 12. The dichroic mirror 17 is disposed on the third optical path OP3. The illumination light L1, the illumination light L2, the illumination light L3, and the illumination light L4 are incident on the dichroic mirror 17.

The wavelength band of the illumination light L1, the wavelength band of the illumination light L2, and the wavelength band of the illumination light L3 are located on the shorter wavelength side than the wavelength band of the illumination light L4. The dichroic mirror 17 has a characteristic of transmitting light with short wavelengths and reflecting light with long wavelengths. The illumination light L1, the illumination light L2, and the illumination light L3 are transmitted through the dichroic mirror 17, and the illumination light L4 is reflected by the dichroic mirror 17.

In the dichroic mirror 17, the illumination light L1, the illumination light L2, the illumination light L3, and the illumination light L4 are combined. As a result, the illumination light L1, the illumination light L2, the illumination light L3, and the illumination light L4 are emitted from the dichroic mirror 17.

In the light source device 10, the illumination light L1, the illumination light L2, the illumination light L3, and the illumination light L4 are combined by the optical system 13. As a result, the illumination light L1, the illumination light L2, the illumination light L3, and the illumination light L4 are emitted from the optical system 13. It is possible to say that the optical system 13 is an optical system that combines the illumination light L1, the illumination light L2, the illumination light L3, and the illumination light L4.

The illumination light L1, the illumination light L2, the illumination light L3, and the illumination light L4 travel through the third optical path OP3. The rotating member 15 is disposed on the emission side of the optical system 13. By rotating the rotating plate 18, it is possible to dispose one of the wavelength selective filter 5 and the parallel flat plate 19 on the third optical path OP3.

The light source device of the second example has a plurality of light emission modes. In the light source device 10, a first light emission mode and a second light emission mode are used.

As illustrated in FIG. 3A, in the first light emission mode, the wavelength selective filter 5 is located on the third optical path OP3. The parallel flat plate 19 is located outside the third optical path OP3. The illumination light L1, the illumination light L2, the illumination light L3, and the illumination light L4 are incident on the wavelength selective filter 5.

As illustrated in FIG. 1B, the wavelength selective filter 5 has the transmission band ΔabT and the transmission band ΔcdT. Therefore, the illumination light L3 and the illumination light L4 are not transmitted through the wavelength selective filter 5. In the first light emission mode, the partial band light L1' and the illumination light L2 are emitted from the wavelength selective filter 5.

As illustrated in FIG. 3B, in the second light emission mode, the parallel flat plate 19 is located on the third optical path OP3. The wavelength selective filter 5 is located outside the third optical path OP3. The illumination light L1, the illumination light L2, the illumination light L3, and the illumination light L4 are incident on the parallel flat plate 19.

A colorless, transparent material is used for the parallel flat plate 19. Therefore, the illumination light L1, the illumination light L2, the illumination light L3, and the illumination light L4 are transmitted through the parallel flat plate 19. In the second light emission mode, the illumination light L1, the illumination light L2, the illumination light L3, and the illumination light L4 are emitted from the parallel flat plate 19.

In this way, the wavelength band of light incident on the rotating member 15 is the same, but the wavelength band of light emitted from the rotating member 15 is different between the first light emission mode and the second light emission mode.

Detection of light emitted from the parallel flat plate 19 may be performed by an optical sensor. However, it is difficult to dispose an optical sensor on the emission side of the parallel flat plate 19. In the light source device 10, the optical sensor 14 is disposed in proximity to the light emitter 2. The optical sensor 14 is disposed at a position where the illumination light L1 reaches. No optical filter is disposed between the light emitter 2 and the optical sensor 14. In this case, part of the illumination light L1 is incident on the optical sensor 14.

As described above, in the light emitter 2, the light quantity of the illumination light L1 decreases as the temperature decreases. As a result, the color balance in illumination light is disturbed in the first light emission mode and the second light emission mode.

In the light source device 10, the optical sensor 6 and the optical filter 7 are used for adjustment in the first light emission mode. The adjustment using the optical sensor 6 and the optical filter 7 has been described in the light source device 1. Therefore, the description of the adjustment in the first light emission mode is omitted.

The adjustment in the second light emission mode will be described. In the description, detection light Ls and emission light Lo are used. The detection light Ls is light detected by the optical sensor 14. The emission light Lo is part of light emitted from the parallel flat plate 19. The detection light Ls and the emission light Lo are not illustrated.

In the second light emission mode, the optical sensor 14 and the parallel flat plate 19 are used. The detection light Ls and the emission light Lo are both illumination light L1. Thus, the wavelength band of the detection light Ls is the same as the wavelength band of the emission light Lo.

When the light quantity of the illumination light L1 changes, the light quantity of the detection light Ls and the light quantity of the emission light Lo change. Therefore, by detecting change in light quantity of the detection light Ls, it is possible to detect change in light quantity of the emission light Lo. In the light source device 10, it is possible to adjust the light quantity in the light emitter 2 based on a signal output from the optical sensor 14.

In the adjustment, the light quantity of the detection light Ls is used. As described above, the wavelength band of the detection light Ls is the same as the wavelength band of the emission light Lo. In this case, adjustment is performed for the light emitter 2, using the same light as the light emitted from the parallel flat plate 19. Thus, when the light quantity in the light emitter 2 changes, it is possible to maintain the ideal color balance by performing adjustment. As a result, in the second light emission mode, illumination light suitable for observation can be obtained.

In the light source device 10, it is possible to use an LED as a light emitter. For example, it is possible to use an LED emitting violet light for the light emitter 2, an LED emitting blue light for the light emitter 3, an LED emitting green light for the light emitter 11, and an LED emitting red light for the light emitter 12.

In the first light emission mode, illumination light consists of violet light and blue light in a narrow band. Therefore, illumination light suitable for narrow-band light observation can be obtained. In the second light emission mode, illumination light consists of violet light, blue light, green light, and red light. Therefore, illumination light suitable for normal observation can be obtained. Illumination light consisting of blue light, green light, and red light may be used as illumination light suitable for normal observation.

In this way, the light source device 10 has a plurality of light emission modes. In the light emission modes, light in a different wavelength band is emitted in each of the light emission modes. In the light source device 10, a wavelength selective filter is disposed on an optical path in one of the light emission modes.

In the light source device 10, the optical sensor 6 and the optical sensor 14 are used. Therefore, the light source device 10 includes a plurality of optical sensors. Since the optical sensor 6 and the optical sensor 14 receive light from the light emitter 2, the optical sensors receive light from one light emitter. Since the wavelength bands of light received by the optical sensor 6 and the optical sensor 14 are different from each other, the wavelength bands of light received by the optical sensors are different from each other.

In the light source device 10, the optical filter 7 is used. However, instead of the optical filter 7, the optical filter 8 illustrated in FIG. 2 may be used.

Figure 4:
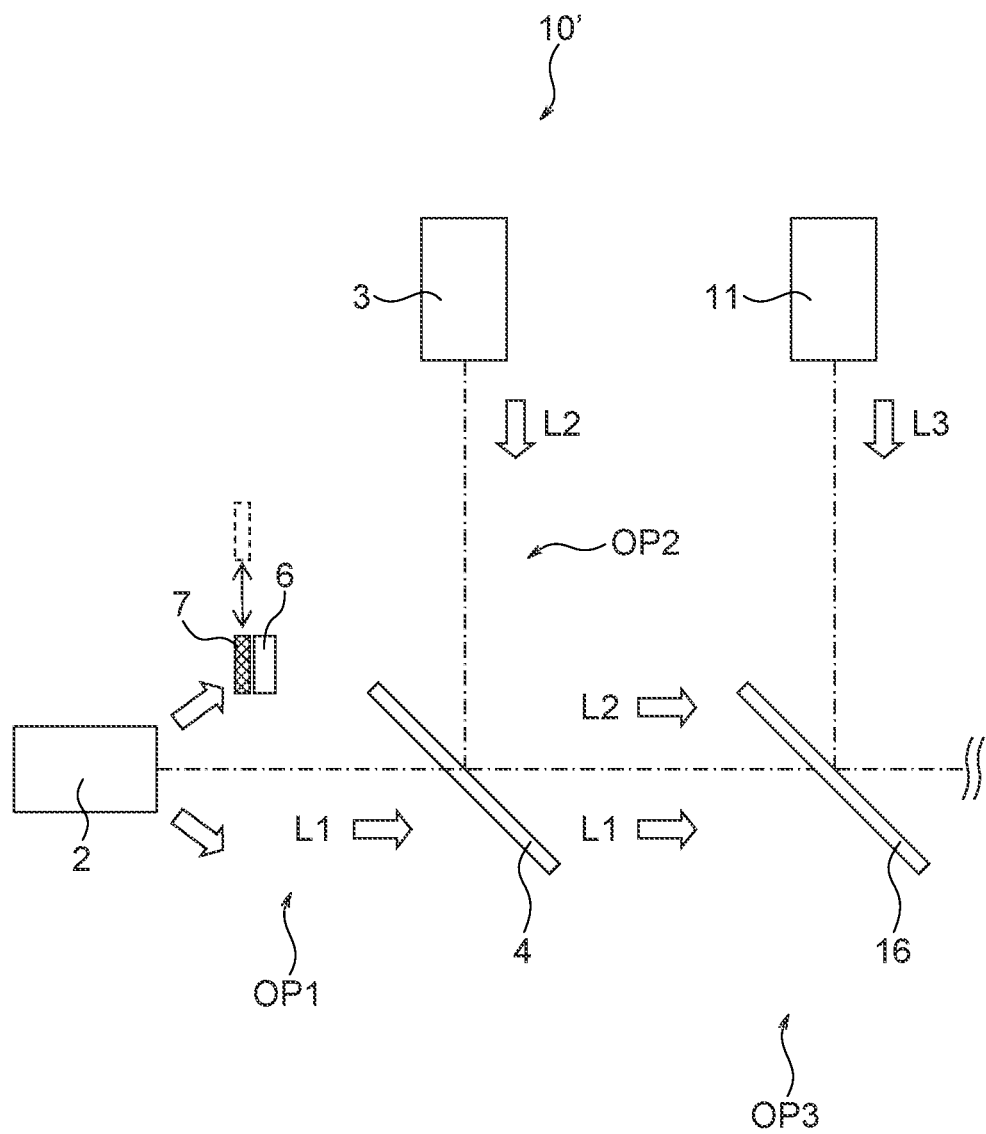
FIG. 4 is a diagram illustrating a second modification of the light source device.

FIG. 4 is a diagram illustrating a second modification of the light source device. The same component as in FIG. 3A is denoted by the same number and a description thereof will be omitted.

In a light source device 10', the optical filter 7 moves. The movement of the optical filter 7 may be performed by translation or rotation.

In the first light emission mode, the optical filter 7 is located in front of the optical sensor 6. The description of the adjustment in the first light emission mode is omitted.

In the second light emission mode, the optical filter 7 moves to a position indicated by a broken line. Since the optical filter 7 is not located in front of the optical sensor 6, it is possible to consider the optical sensor 6 as the optical sensor 14 in the light source device 10. The description of the adjustment in the second light emission mode is omitted.

A parallel flat plate may be disposed at the position indicated by the broken line. The material of the parallel flat plate may be the same as the material of the parallel flat plate 19. In this case, light reception by the optical sensor 6 is performed by switching between the optical filter 7 and the parallel flat plate.

When the parallel flat plate is considered as an optical filter, the light source device 10' includes a plurality of optical filters. Since the wavelength selection characteristic of the optical filter 7 and the wavelength selection characteristic of the parallel flat plate are different, the wavelength selection characteristics of a plurality of optical filters are different from each other. Since the optical filter 7 and the parallel flat plate are switched in light reception, a plurality of optical filters are switched and light is received by the optical sensor.

Figure 5A:
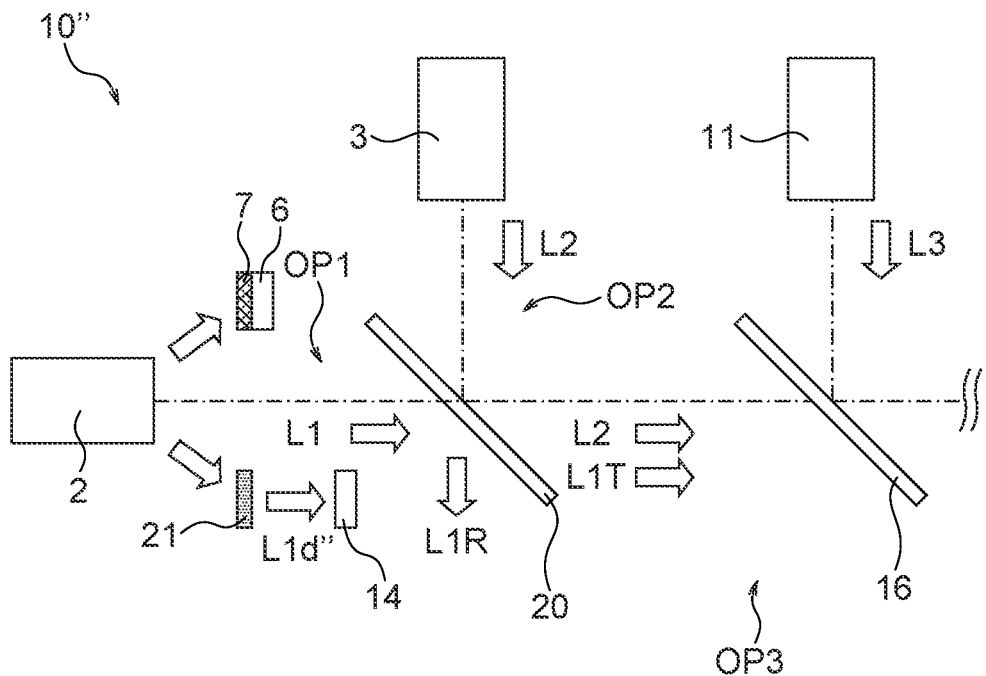
FIGS. 5A, 5B, and 5C are diagrams illustrating a third modification of the light source device, the wavelength band of illumination light, and the wavelength selection characteristic of a dichroic mirror.
Figure 5B:
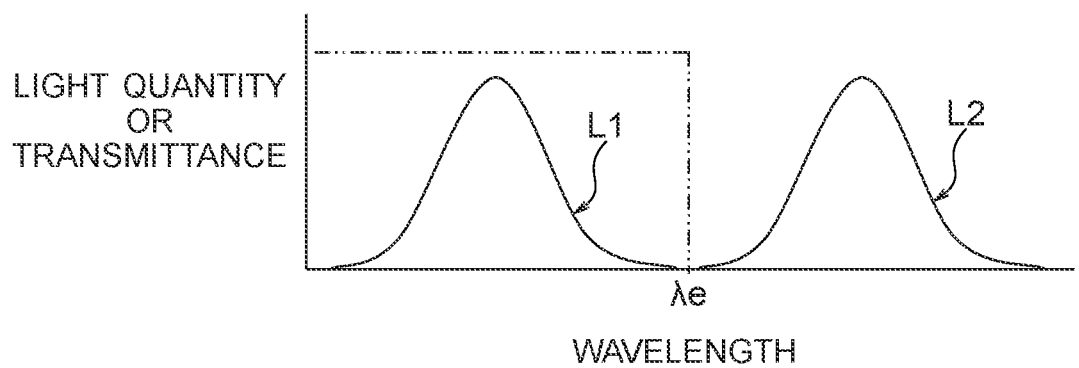
Figure 5C:
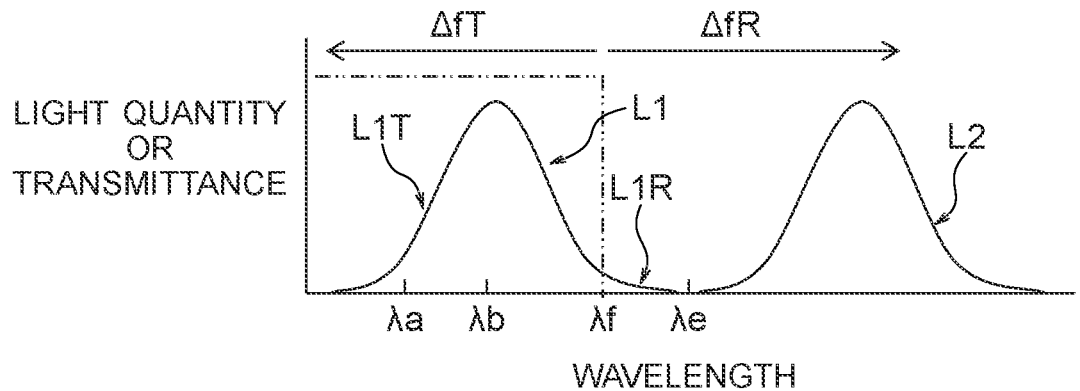

FIGS. 5A, 5B, and 5C are diagrams illustrating a third modification of the light source device, the wavelength band of illumination light, and the wavelength selection characteristic of a dichroic mirror. FIG. 5A is a diagram illustrating the third modification of the light source device. FIGS. 5B and 5C are diagrams illustrating the wavelength band of illumination light and the wavelength selection characteristic of a dichroic mirror. The same component as in FIG. 3A is denoted by the same number and a description thereof will be omitted.

As illustrated in FIG. 5A, a light source device 10" includes a dichroic mirror 20 and an optical filter 21.

The optical filter 21 is adjacent to the optical sensor 14. In FIG. 5A, the optical filter 21 is separated from the optical sensor 14 for the sake of visibility. The optical filter 21 is disposed between the light emitter 2 and the optical sensor 14. The optical filter 21 is a transmissive optical filter.

In the light source device 10 and the light source device 10", the wavelength selective filter 5 and the parallel flat plate 19 are used. However, the dichroic mirror 4 is used in the light source device 10, whereas the dichroic mirror 20 is used in the light source device 10". The description will be given in comparison with the dichroic mirror 4.

The case where the dichroic mirror 4 is used (hereinafter referred to as "case D4") will be described. In FIG. 5B, the wavelength band of the illumination light L1 and the wavelength band of the illumination light L2 are depicted by solid lines. Further, the wavelength selection characteristic of the dichroic mirror 4 is depicted by a chain double-dashed line. The horizontal axis indicates wavelength. The vertical axis indicates light quantity or transmittance.

The dichroic mirror 4 has a characteristic of transmitting light shorter than a wavelength $\lambda e$ and reflecting light longer than the wavelength $\lambda e$. In the illumination light L1, the entire wavelength band is located on the shorter wavelength side than the wavelength $\lambda e$. Therefore, in the illumination light L1, all of the light in the wavelength band is emitted from the dichroic mirror 4.

A case where the dichroic mirror 20 is used (hereinafter referred to as "case D20") will be described. In FIG. 5C, the wavelength band of the illumination light L1 and the wavelength band of the illumination light L2 are depicted by solid lines. Further, the wavelength selection characteristic of the dichroic mirror 20 is depicted by a chain double-dashed line. The horizontal axis indicates wavelength. The vertical axis indicates light quantity or transmittance.

The dichroic mirror 20 has a characteristic of transmitting light shorter than a wavelength $\lambda f$ and reflecting light longer than the wavelength $\lambda f$. The wavelength band of a transmission band $\Delta fT$ is on the shorter wavelength side than the wavelength $\lambda f$. The wavelength band of a reflection band $\Delta fR$ is on the longer wavelength side than the wavelength $\lambda f$.

Illumination light L1 is divided into partial band light L1T and partial band light L1R. The wavelength band of the partial band light L1T is included in the transmission band $\Delta fT$. The wavelength band of the partial band light L1R is included in the reflection band $\Delta fR$. Therefore, the partial band light L1T is emitted from the dichroic mirror 20, but the partial band light L1R is not emitted from the dichroic mirror 20.

In this way, the wavelength band of light emitted from the dichroic mirror differs between the case D4 and the case D20. On the wavelength selective filter 5 and the parallel flat plate 19, the illumination light L1 is incident in the case D4, and the partial band light L1T is incident in the case D20.

In the first light emission mode, the wavelength selective filter 5 is used. The wavelength band from the wavelength $\lambda a$ to the wavelength $\lambda b$ is included in the wavelength band of the illumination light L1 and the wavelength band of the partial band light L1T. Therefore, ether in the case D4 or in the case D20, the partial band light L1' is emitted from the wavelength selective filter 5.

In this case, the light emitted from the wavelength selective filter 5 is the same either in the case D4 or in the case D20. In this case, the light detected by the optical sensor 6 does not have to be different either in the case D4 or in the case D20. Therefore, in the light source device 10", the optical filter 7 is used for detection by the optical sensor 6, in the same manner as in the light source device 10.

In the second light emission mode, the parallel flat plate 19 is used. A colorless, transparent material is used for the parallel flat plate 19. Therefore, from the parallel flat plate 19, the illumination light L1 is emitted in the case D4, whereas the partial band light L1T is emitted in the case D20.

In this way, the light emitted from the parallel flat plate 19 is different between the case D4 and the case D20. In this case, the light detected by the optical sensor 14 needs to be different between the case D4 and the case D20.

Thus, in the light source device 10", unlike the light source device 10, light is not detected only by the optical sensor 14 but light is detected through the optical filter 21. The transmission band of the optical filter 21 is the same as the wavelength band of the transmission band ΔfT.

Detection light L1d'" is detected in the optical sensor 14. The detection light L1d'" is light transmitted through the optical filter 21. Only the illumination light L1 is incident on the optical filter 21. In this case, the wavelength band of the detection light L1d'" is the same as the transmission band ΔfT. The transmission band ΔfT is the same as the wavelength band of the partial band light L1T. Therefore, the wavelength band of the detection light L1d'" is the same as the wavelength band of the partial band light L1T.

When the light quantity of the illumination light L1 changes, the light quantity of the detection light L1d'" and the light quantity of the partial band light L1T change. Therefore, by detecting change in light quantity of the detection light L1d'", it is possible to detect change in light quantity of the partial band light L1T. In the light source device 10", it is possible to adjust the light quantity in the light emitter 2 based on a signal output from the optical sensor 14.

In the adjustment, the light quantity of the detection light L1d'" is used. As described above, the wavelength band of the detection light L1d'" is the same as the wavelength band of the partial band light L1T. In this case, adjustment is performed for the light emitter 2, using the same light as the light emitted from the parallel flat plate 19. Thus, when the light quantity in the light emitter 2 changes, it is possible to maintain the ideal color balance by performing adjustment. As a result, in the second light emission mode, illumination light suitable for observation can be obtained.

When the optical filter 21 is not disposed, the light quantity of the illumination light L1 is used in the adjustment. In this case, adjustment is performed for the light emitter 2, using light different from the light emitted from the parallel flat plate 19. Thus, when the light quantity in the light emitter 2 changes, it is impossible to maintain the ideal color balance even by performing adjustment. As a result, in the second light emission mode, illumination light suitable for observation is unable to be obtained.

Only partial light of the illumination light L1 is incident on the optical sensor 14. In this case, the light quantity of light detected by the optical sensor 14 and the light quantity of light emitted from the parallel flat plate 19 are different. Therefore, adjustment in the light emitter 2 may be performed in consideration of the difference in light quantity between the two types of light.

Figure 6A:
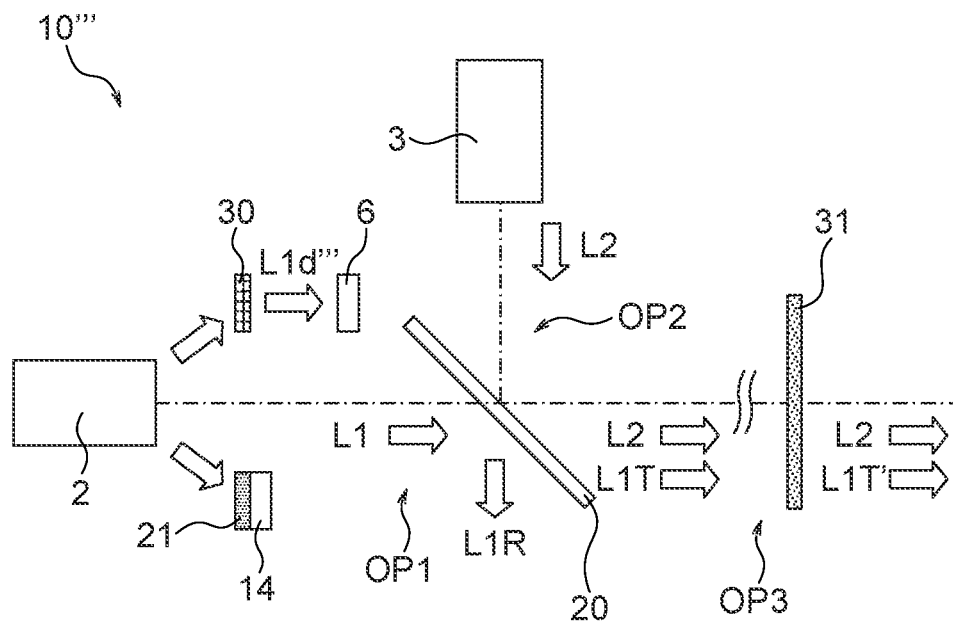
FIGS. 6A and 6B are diagrams illustrating a fourth modification of the light source device, the wavelength band of illumination light, the wavelength selection characteristic of a wavelength selective filter, and the wavelength selection characteristic of a dichroic mirror.
Figure 6B:
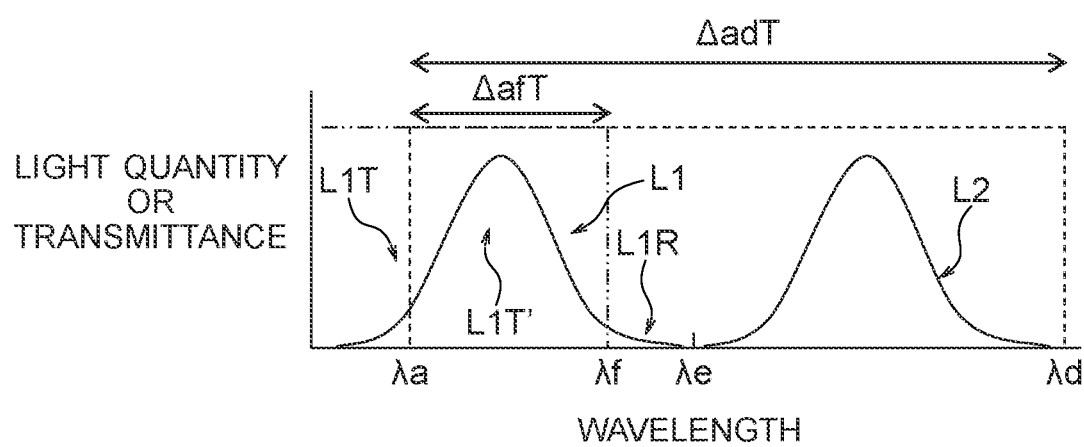

FIGS. 6A and 6B are diagrams illustrating a fourth modification of the light source device, the wavelength band of illumination light, the wavelength selection characteristic of a wavelength selective filter, and the wavelength selection characteristic of a dichroic mirror. FIG. 6A is a diagram illustrating the fourth modification of the light source device. FIG. 6B is a diagram illustrating the wavelength band of illumination light, the wavelength selection characteristic of a wavelength selective filter, and the wavelength selection characteristic of a dichroic mirror. The same component as in FIG. 5A is denoted by the same number and a description thereof will be omitted.

In the light source device described above, partial band light L1' is emitted from the wavelength selective filter 5. The wavelength band of the partial band light L1' is the same as the transmission band ΔabT. The transmission band ΔabT is the transmission band in the wavelength selective filter 5. Therefore, the wavelength band of the partial band light L1' is determined only by the transmission band of the wavelength selective filter 5.

However, it is also possible to determine the wavelength band of light emitted from the wavelength selective filter by the transmission band of the wavelength selective filter and the transmission band of the dichroic mirror.

As illustrated in FIG. 6A, a light source device 10'" includes an optical filter 30 and a wavelength selective filter 31. The optical filter 30 is adjacent to the optical sensor 6. The optical filter 30 is a transmissive optical filter. The wavelength selective filter 31 is located on the optical path OP3.

In FIG. 6B, the wavelength band of the illumination light L1 and the wavelength band of the illumination light L2 are depicted by solid lines. Further, the wavelength selection characteristic of the dichroic mirror 20 is depicted by a chain double-dashed line, and the wavelength selection characteristic of the wavelength selective filter 31 is depicted by a broken line. The horizontal axis indicates wavelength. The vertical axis indicates light quantity or transmittance.

As described above, the dichroic mirror 20 has a characteristic of transmitting light shorter than a wavelength λf and reflecting light longer than the wavelength λf. Therefore, in the illumination light L1, partial band light L1T is transmitted through the dichroic mirror 20, and partial band light L1R is reflected by the dichroic mirror 20. As a result, the partial band light L1T is emitted from the dichroic mirror 20, but the partial band light L1R is not emitted from the dichroic mirror 20.

The partial band light L1T travels through the third optical path OP3. The wavelength selective filter 31 is disposed on the emission side of the dichroic mirror 20. The partial band light L1T is incident on the wavelength selective filter 31. The wavelength selective filter 31 has a transmission band ΔadT. The wavelength band of the transmission band ΔadT is from a wavelength λa to a wavelength λd.

Light from the wavelength λa to the wavelength λf is defined as partial band light L1T'. The wavelength band of the partial band light L1T' is from the wavelength λa to the wavelength λf. The wavelength band of the partial band light L1T' is the same as a transmission band ΔafT. The transmission band ΔafT is included in the transmission band ΔadT. Therefore, the partial band light L1T' is emitted from the wavelength selective filter 31.

In the transmission band ΔafT, the wavelength λa is determined by the transmission band of the wavelength selective filter 31. The wavelength λf is determined by the transmission band of the dichroic mirror 20. In this way, in the light source device 10''', the wavelength band of light emitted from the wavelength selective filter 31 is determined by the transmission band of the wavelength selective filter 31 and the transmission band of the dichroic mirror 20.

The adjustment in the first light emission mode will be described. In the first light emission mode, the wavelength selective filter 31 is used. In this case, partial band light L1T' is emitted from the wavelength selective filter 31. To maintain the ideal color balance, change in light quantity of the partial band light L1T' may be detected, and the light quantity of the light emitter 2 may be adjusted based on the detected result.

In the light source device 10''', light is detected through the optical filter 30. It is only necessary that the wavelength band of light emitted from the optical filter 30 should correspond to the wavelength band of the partial band light L1T'. Specifically, the optical filter 30 has a wavelength selection characteristic such that the transmission band is identical to the transmission band ΔafT.

Detection light L1d''' is detected in the optical sensor 6. The detection light L1d''' is light transmitted through the optical filter 30. Only the illumination light L1 is incident on the optical filter 30. In this case, the wavelength band of the detection light L1d''' is the same as the transmission band αafT. The transmission band αafT is the same as the wavelength band of the partial band light L1T'. Therefore, the wavelength band of the detection light L1d''' is the same as the wavelength band of the partial band light L1T'.

When the light quantity of the illumination light L1 changes, the light quantity of the detection light L1d''' and the light quantity of the partial band light L1T' change. Therefore, by detecting change in light quantity of the detection light L1d''', it is possible to detect change in light quantity of the partial band light L1T'. In the light source device 10''', it is possible to adjust the light quantity in the light emitter 2 based on a signal output from the optical sensor 6.

In the adjustment, the light quantity of the detection light L1d''' is used. As described above, the wavelength band of the detection light L1d''' is the same as the wavelength band of the partial band light L1T'. In this case, adjustment is performed for the light emitter 2, using the same light as the light emitted from the wavelength selective filter 31. Thus, when the light quantity in the light emitter 2 changes, it is possible to maintain the ideal color balance by performing adjustment. As a result, in the first light emission mode, illumination light suitable for observation can be obtained.

In the adjustment in the second light emission mode, the optical sensor 14 and the optical filter 21 are used. The adjustment using the optical sensor 14 and the optical filter 21 has been described in the light source device 10''. Therefore, the description of the adjustment in the second light emission mode is omitted.

The transmission band of the optical filter 30 is the same as the wavelength band of the transmission band ΔafT. The transmission band ΔafT is included in the transmission band ΔadT. Therefore, the optical filter 30 has a wavelength selection characteristic corresponding to the wavelength selection characteristic of the wavelength selective filter 31.

The optical filter 30 is formed with one optical member, but may be formed with two optical members. In this case, one optical member may have the same wavelength band as the transmission band of the wavelength selective filter 31, and the other optical member may have the same wavelength band as the wavelength selection characteristic of the dichroic mirror 20.

In this case, one optical member has the same wavelength band as the transmission band of the wavelength selective filter 31. Therefore, even when the optical filter is formed with two members, the optical filter has a wavelength selection characteristic corresponding to the wavelength selection characteristic of the wavelength selective filter 31.

In the light source device 10''', for the illumination light L1, the wavelength band of light emitted from the wavelength selective filter is determined by the transmission band of the wavelength selective filter and the transmission band of the dichroic mirror. For the illumination light L2, it is also possible to determine the wavelength band of light emitted from the wavelength selective filter by the transmission band of the wavelength selective filter and the transmission band of the dichroic mirror.

Figure 7A:
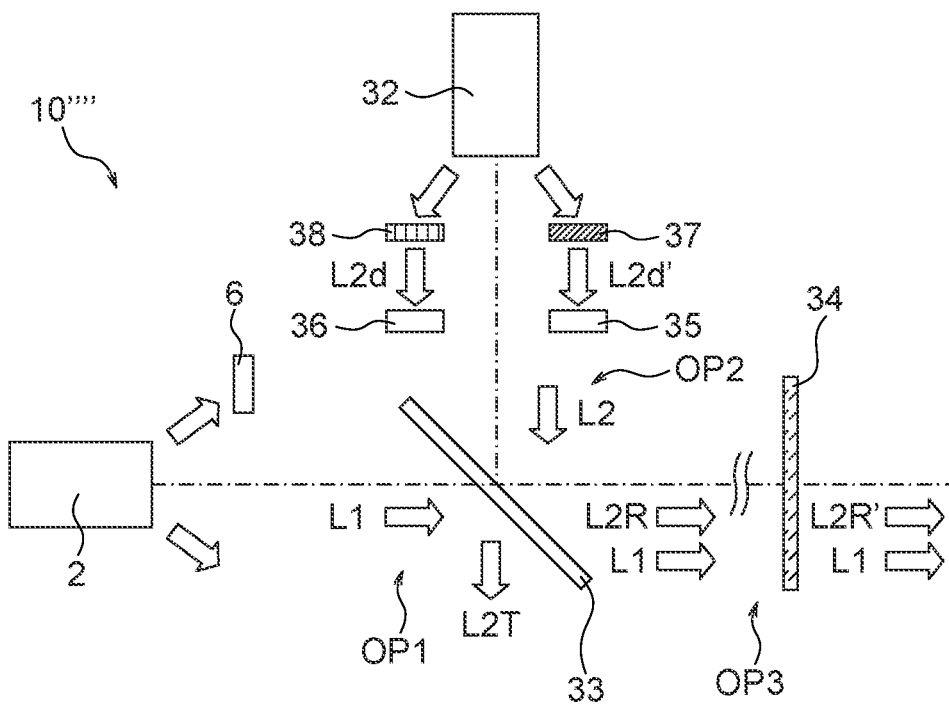
FIGS. 7A and 7B are diagrams illustrating a fifth modification of the light source device, the wavelength band of illumination light, the wavelength selection characteristic of a wavelength selective filter, and the wavelength selection characteristic of a dichroic mirror.
Figure 7B:
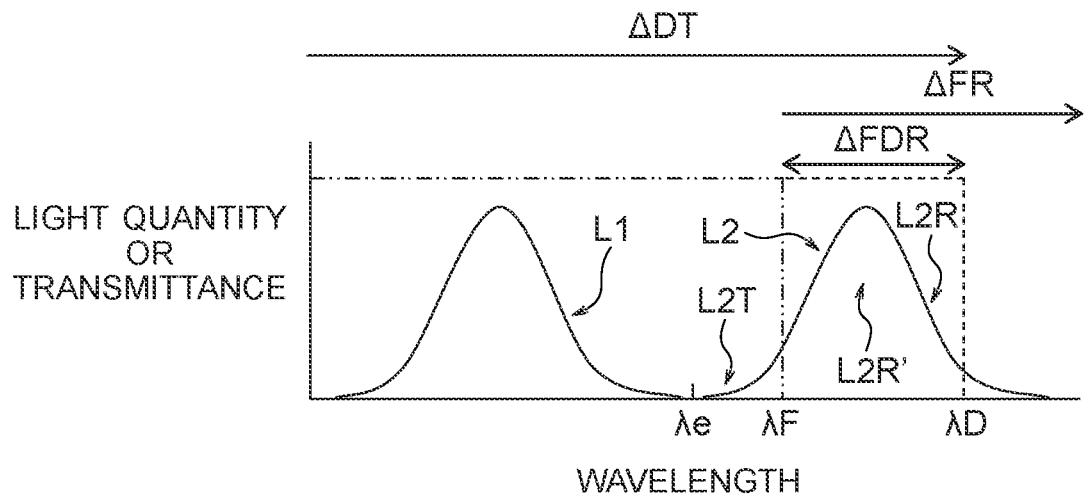

FIGS. 7A and 7B are diagrams illustrating a fifth modification of the light source device, the wavelength band of illumination light, the wavelength selection characteristic of a wavelength selective filter, and the wavelength selection characteristic of a dichroic mirror. FIG. 7A is a diagram illustrating the fifth modification of the light source device. FIG. 7B is a diagram illustrating the wavelength band of illumination light, the wavelength selection characteristic of a wavelength selective filter, and the wavelength selection characteristic of a dichroic mirror. The same component as in FIG. 5A is denoted by the same number and a description thereof will be omitted.

As illustrated in FIG. 7A, a light source device 10'''' includes a light emitter 32, a dichroic mirror 33, a wavelength selective filter 34, an optical sensor 35, an optical sensor 36, an optical filter 37, and an optical filter 38.

The dichroic mirror 33 is disposed at the position where the first optical path OP1 and the second optical path OP2 intersect. The wavelength selective filter 34 is located on the optical path OP3.

In FIG. 7B, the wavelength band of the illumination light L1 and the wavelength band of the illumination light L2 are depicted by solid lines. Further, the wavelength selection characteristic of the dichroic mirror 33 is depicted by a chain double-dashed line, and the wavelength selection characteristic of the wavelength selective filter 34 is depicted by a broken line. The horizontal axis indicates wavelength. The vertical axis indicates light quantity or transmittance.

The dichroic mirror 33 has a characteristic of transmitting light shorter than a wavelength λF and reflecting light longer than the wavelength λF. Therefore, in the illumination light L2, partial band light L2R is reflected by the dichroic mirror 33, and partial band light L2T is transmitted through the dichroic mirror 33. As a result, the partial band light L2R is emitted from the dichroic mirror 33, but the partial band light L2T is not emitted from the dichroic mirror 33.

The partial band light L2R travels through the third optical path OP3. The wavelength selective filter 34 is disposed on the emission side of the dichroic mirror 33. The partial band light L2R is incident on the wavelength selective filter 34. The wavelength selective filter 34 has a transmission band ΔDT. The wavelength band of the transmission band ΔDT is on the shorter wavelength side than a wavelength λD.

Light from the wavelength λF to the wavelength λD is defined as partial band light L2R'. The wavelength band of the partial band light L2R' is from the wavelength λF to the wavelength λD. The wavelength band of the partial band light L2R' is the same as a reflection band ΔFDR. The reflection band ΔFDR is included in the transmission band ΔDT. Therefore, the partial band light L2R' is emitted from the wavelength selective filter 34.

In the reflection band ΔFDR, the wavelength 2F is determined by the reflection band of the dichroic mirror 33. The wavelength λD is determined by the transmission band of the wavelength selective filter 34. In this way, in the light source device 10'''', the wavelength band of light emitted from the wavelength selective filter 34 is determined by the reflection band of the dichroic mirror 33 and the transmission band of the wavelength selective filter 34.

In the light emitter 2 and the light emitter 32, the light quantity changes with temperature. Therefore, it is necessary to adjust the light quantity of the light emitter 2 and the light quantity of the light emitter 32.

The adjustment in the light emitter 2 will be described. In the light emitter 2, illumination light L1 is incident on the wavelength selective filter 34 and the parallel flat plate 19. The entire wavelength band of the illumination light L1 is included in the transmission band of the wavelength selective filter 34 and the transmission band of the parallel flat plate 19. In this case, light in the entire wavelength band of the illumination light L1 is emitted from the rotating member 15 in both of the first light emission mode and the second light emission mode. Therefore, to maintain the ideal color balance, change in light quantity of the illumination light L1 may be detected, and the light quantity of the light emitter 2 may be adjusted based on the detected result.

In the light source device 10'''', the optical sensor 6 is disposed in proximity to the light emitter 2. Part of the illumination light L1 is incident on the optical sensor 6. In this case, adjustment is performed for the light emitter 2, using the same light as the light emitted from the wavelength selective filter 34. Thus, when the light quantity in the light emitter 2 changes, it is possible to maintain the ideal color balance by performing adjustment. As a result, in the first light emission mode, illumination light suitable for observation can be obtained.

The adjustment in the light emitter 32 will be described. In the light emitter 32, partial band light L2R is incident on the wavelength selective filter 34 and the parallel flat plate 19. The entire wavelength band of the partial band light L2R is not included in the transmission band of the wavelength selective filter 34. The entire wavelength band of the partial band light L2R is included in the transmission band of the parallel flat plate 19. In this case, the wavelength band of light emitted from the rotating member 15 is different between the first light emission mode and the second light emission mode.

The adjustment in the first light emission mode will be described. In the first light emission mode, the wavelength selective filter 34 is used. In this case, partial band light L2R' is emitted from the wavelength selective filter 34. To maintain the ideal color balance, change in light quantity of the partial band light L2R' may be detected, and the light quantity of the light emitter 32 may be adjusted based on the detected result.

Detection of the partial band light L2R' may be performed by an optical sensor. However, it is difficult to dispose an optical sensor on the emission side of the wavelength selective filter 34. In the light source device 10'''', the optical sensor 35 and the optical filter 37 are disposed in proximity to the light emitter 32. It is only necessary that the wavelength band of light emitted from the optical filter 37 should correspond to the wavelength band of the partial band light L2R'.

The optical sensor 35 receives light from the light emitter 32 through the optical filter 37. The illumination light L2 is emitted from the light emitter 32. The optical sensor 35 is disposed at a position where the illumination light L2 reaches.

The optical filter 37 is adjacent to the optical sensor 35. In FIG. 7A, the optical filter 37 is separated from the optical sensor 35 for the sake of visibility. The optical filter 37 is disposed between the light emitter 32 and the optical sensor 35. The optical filter 37 is a transmissive optical filter.

The optical filter 37 has a wavelength selection characteristic corresponding to the wavelength selection characteristic of the wavelength selective filter 34. Specifically, the optical filter 37 has a wavelength selection characteristic such that the transmission band is identical to the reflection band ΔFDR.

Detection light L2d' is detected in the optical sensor 35. The detection light L2d' is light transmitted through the optical filter 37. Only the illumination light L2 is incident on the optical filter 37. In this case, the wavelength band of the detection light L2d' is the same as the reflection band ΔFDR. The reflection band ΔFDR is the same as the wavelength band of the partial band light L2R'. Therefore, the wavelength band of the detection light L2d' is the same as the wavelength band of the partial band light L2R'.

When the light quantity of the illumination light L2 changes, the light quantity of the detection light L2d' and the light quantity of the partial band light L2R' change. Therefore, by detecting change in light quantity of the detection light L2d', it is possible to detect change in light quantity of the partial band light L2R'. In the light source device 10'''', it is possible to adjust the light quantity in the light emitter 32 based on a signal output from the optical sensor 35.

In the adjustment, the light quantity of the detection light L2d' is used. As described above, the wavelength band of the detection light L2d' is the same as the wavelength band of the partial band light L2R'. In this case, adjustment is performed for the light emitter 32, using the same light as the light emitted from the wavelength selective filter 34. Thus, when the light quantity in the light emitter 32 changes, it is possible to maintain the ideal color balance by performing adjustment. As a result, in the first light emission mode, illumination light suitable for observation can be obtained.

The optical filter 37 is formed with one optical member, but may be formed with two optical members. In this case, one optical member may have the same wavelength band as the transmission band of the wavelength selective filter 34, and the other optical member may have the same wavelength band as the wavelength selection characteristic of the dichroic mirror 33.

In this case, one optical member has the same wavelength band as the transmission band of the wavelength selective filter 34. Therefore, even when the optical filter is formed with two members, the optical filter has a wavelength selection characteristic corresponding to the wavelength selection characteristic of the wavelength selective filter 34.

The adjustment in the second light emission mode will be described. In the second light emission mode, the parallel flat plate 19 is used. In this case, partial band light L2R is emitted from the parallel flat plate 19. To maintain the ideal color balance, change in light quantity of the partial band light L2R may be detected, and the light quantity of the light emitter 32 may be adjusted based on the detected result.

Detection of the partial band light L2R may be performed by an optical sensor. However, it is difficult to dispose an optical sensor on the emission side of the parallel flat plate 19. In the light source device 10'''', the optical sensor 36 and the optical filter 38 are disposed in proximity to the light emitter 32. It is only necessary that the wavelength band of light emitted from the optical filter 38 should correspond to the wavelength band of the partial band light L2R.

The optical sensor 36 receives light from the light emitter 32 through the optical filter 38. The illumination light L2 is emitted from the light emitter 32. The optical sensor 36 is disposed at a position where the illumination light L2 reaches.

The optical filter 38 is adjacent to the optical sensor 36. In FIG. 7A, the optical filter 38 is separated from the optical sensor 36 for the sake of visibility. The optical filter 38 is disposed between the light emitter 32 and the optical sensor 36. The optical filter 38 is a transmissive optical filter. The optical filter 38 has a wavelength selection characteristic such that the transmission band is the same as the reflection band ΔFR.

Detection light L2d is detected in the optical sensor 36. The detection light L2d is light transmitted through the optical filter 38. Only the illumination light L2 is incident on the optical filter 38. In this case, the wavelength band of the detection light L2d is included in the reflection band ΔFR. The reflection band ΔFR includes the wavelength band of the partial band light L2R. Therefore, the wavelength band of the detection light L2d is the same as the wavelength band of the partial band light L2R'.

When the light quantity of the illumination light L2 changes, the light quantity of the detection light L2d and the light quantity of the partial band light L2R change. Therefore, by detecting change in light quantity of the detection light L2d, it is possible to detect change in light quantity of the partial band light L2R. In the light source device 10'''', it is possible to adjust the light quantity in the light emitter 32 based on a signal output from the optical sensor 36.

In the adjustment, the light quantity of the detection light L2d is used. As described above, the wavelength band of the detection light L2d is the same as the wavelength band of the partial band light L2R. In this case, adjustment is performed for the light emitter 32, using the same light as the light emitted from the parallel flat plate 19. Thus, when the light quantity in the light emitter 32 changes, it is possible to maintain the ideal color balance by performing adjustment. As a result, in the second light emission mode, illumination light suitable for observation can be obtained.

Figure 8A:
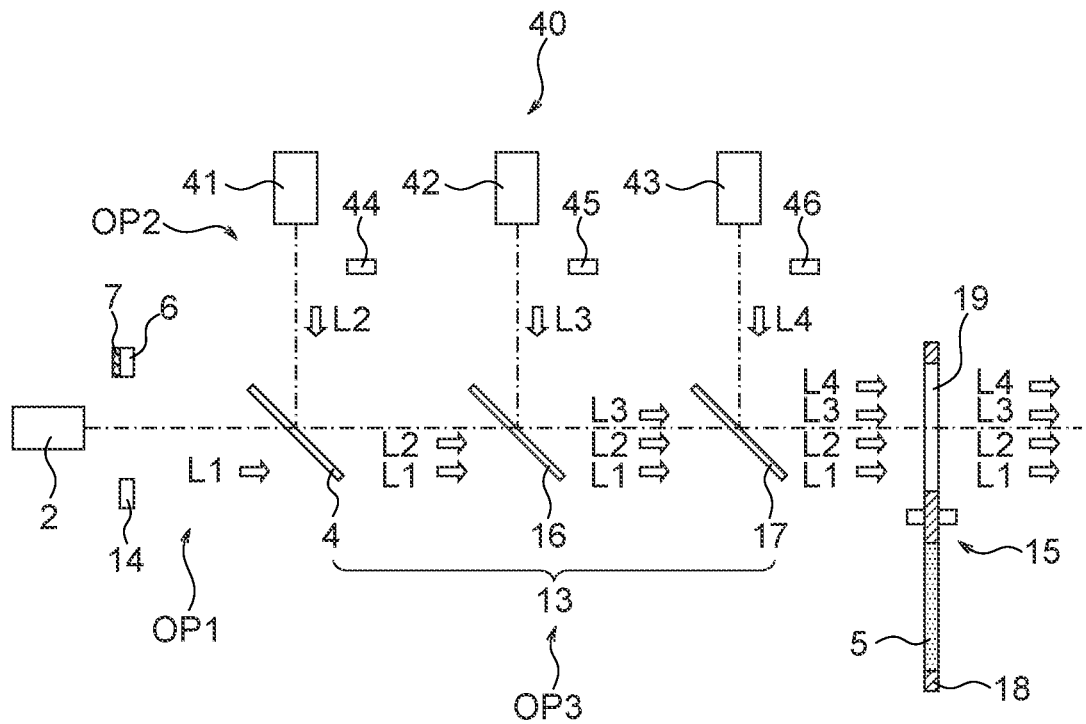
FIGS. 8A and 8B are diagrams illustrating a light source device of the present embodiment.
Figure 8B:
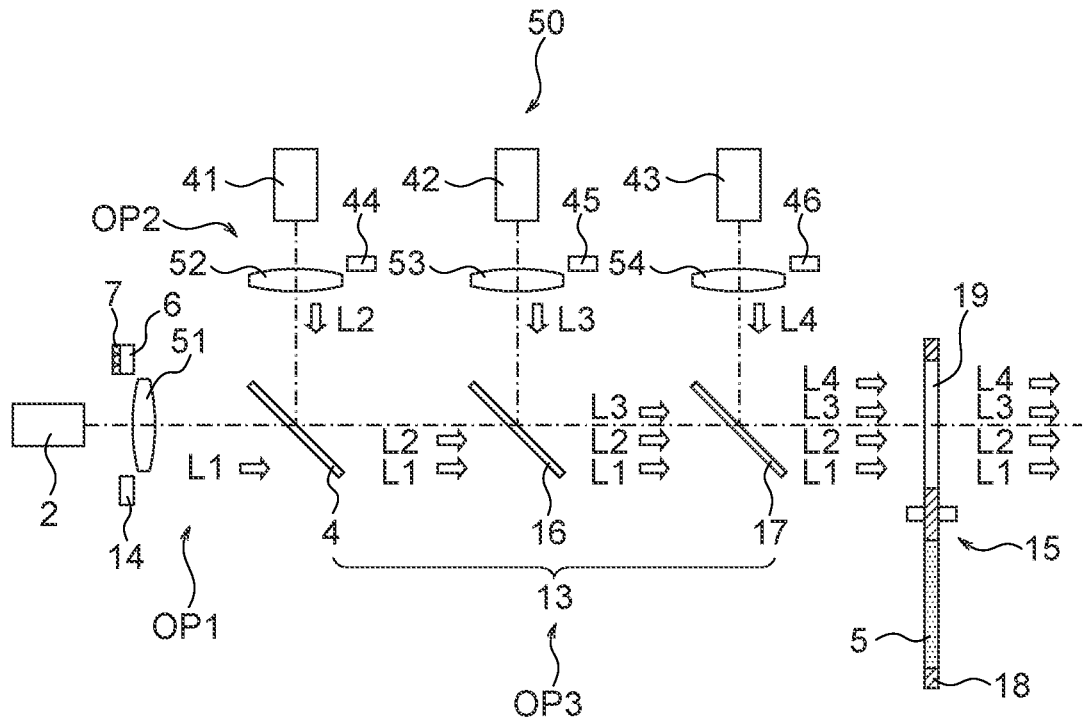

FIGS. 8A and 8B are diagrams illustrating a light source device of the present embodiment. FIG. 8A is a diagram illustrating a third example of the light source device of the present embodiment. FIG. 8B is a diagram illustrating a fourth example of the light source device of the present embodiment. The same component as in FIG. 3A is denoted by the same number and a description thereof will be omitted.

The light source device of the third example will be described. The light source device of the third example includes four light emitters. In the light source device of the third example, the light quantity in the four light emitters changes with temperature.

As illustrated in FIG. 8A, a light source device 40 includes a light emitter 2, a light emitter 41, a light emitter 42, and a light emitter 43. In the light emitter 2, the light emitter 41, the light emitter 42, and the light emitter 43, the light quantity changes with temperature.

The light source device 40 includes an optical sensor 14, an optical sensor 44, an optical sensor 45, and an optical sensor 46.

The optical sensor 44 is disposed in proximity to the light emitter 41. The optical sensor 44 receives part of the illumination light L2. No optical filter is disposed between the light emitter 41 and the optical sensor 44. Therefore, the optical sensor 44 receives partial light of the illumination light L2 as it is.

The optical sensor 45 is disposed in proximity to the light emitter 42. The optical sensor 45 receives part of the illumination light L3. No optical filter is disposed between the light emitter 42 and the optical sensor 45. Therefore, the optical sensor 45 receives partial light of the illumination light L3 as it is.

The optical sensor 46 is disposed in proximity to the light emitter 43. The optical sensor 46 receives part of the illumination light L4. No optical filter is disposed between the light emitter 43 and the optical sensor 46. Therefore, the optical sensor 46 receives partial light of the illumination light L4 as it is.

In the light source device 40, it is possible to adjust the light quantity in the light emitter 2 based on a signal output from the optical sensor 6, in the same manner as in the light source device 1. Therefore, even when the light quantity in the light emitter 2 changes, it is possible to maintain the ideal color balance by performing adjustment. As a result, in the first light emission mode, illumination light suitable for observation can be obtained.

Further, in the light source device 40, it is possible to adjust the light quantity in the light emitter 2 based on a signal output from the optical sensor 14. It is possible to adjust the light quantity in the light emitter 41 based on a signal output from the optical sensor 44. It is possible to adjust the light quantity in the light emitter 42 based on a signal output from the optical sensor 45. It is possible to adjust the light quantity in the light emitter 43 based on a signal output from the optical sensor 46.

In these adjustments, the light quantity of the illumination light L1, the light quantity of the illumination light L2, the light quantity of the illumination light L3, and the light quantity of the illumination light L4 are used. Therefore, even when the light quantity in the light emitter 2, the light quantity in the light emitter 41, the light quantity in the light emitter 42, and the light quantity in the light emitter 43 change, it is possible to maintain the ideal color balance by performing adjustment. As a result, in the second light emission mode, illumination light suitable for observation can be obtained.

The color of light emitted from each light emitter is set as appropriate, whereby illumination light suitable for narrow-band light observation can be obtained in the first light emission mode, and illumination light suitable for normal observation can be obtained in the second light emission mode, in the same manner as in the light source device 10.

The light source device of the fourth example will be described. The light source device of the fourth example includes four light emitters. In the light source device of the fourth example, the light quantity in the four light emitters changes with temperature.

As illustrated in FIG. 8B, a light source device 50 includes a lens 51, a lens 52, a lens 53, and a lens 54.

The lens 51 is disposed between the light emitter 2 and the dichroic mirror 4. The lens 52 is disposed between the light emitter 41 and the dichroic mirror 4. The lens 53 is disposed between the light emitter 42 and the dichroic mirror 16. The lens 54 is disposed between the light emitter 43 and the dichroic mirror 17.

When illumination light L1, illumination light L2, illumination light L3, and illumination light L4 are divergent light, it is possible to convert the divergent light into parallel light by the lenses. As a result, it is possible to enhance light utilization efficiency. The parallel light includes substantially parallel light.

The light source device 50 includes an optical sensor 6, an optical sensor 14, an optical sensor 44, an optical sensor 45, and an optical sensor 46. Therefore, even in the light source device 50, illumination light suitable for observation can be obtained in the first light emission mode and the second light emission mode in the same manner as in the light source device 40.

Figure 9A:
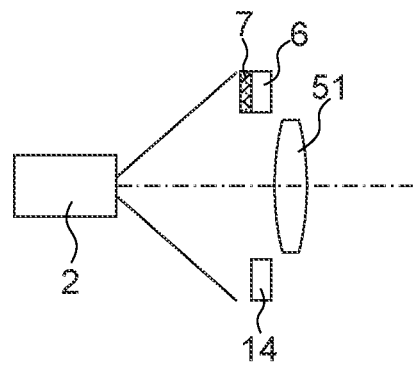
FIGS. 9A, 9B, and 9C are diagrams illustrating an optical sensor arrangement.
Figure 9B:
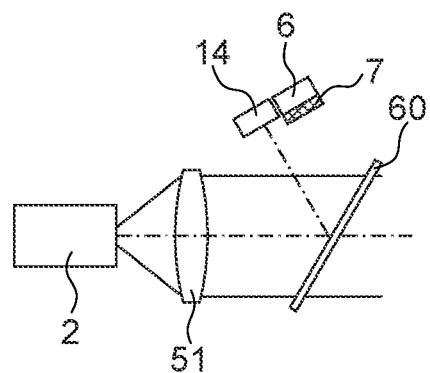
Figure 9C:
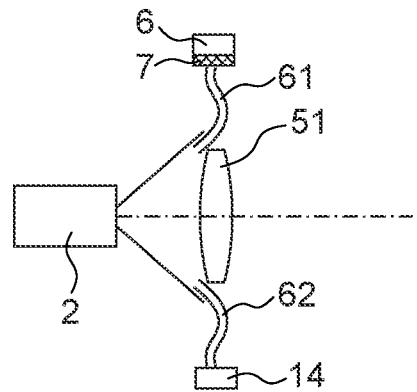

FIGS. 9A, 9B, and 9C are diagrams illustrating an optical sensor arrangement. FIG. 9A is a diagram illustrating a first arrangement example. FIG. 9B is a diagram illustrating a second arrangement example. FIG. 9C is a diagram illustrating a third arrangement example. The same component as in FIG. 3B is denoted by the same number and a description thereof will be omitted.

In any arrangement example, divergent light is emitted from the light emitter 2. The divergent light is incident on the lens 51. Part of the divergent light is detected by the optical sensor 6 and the optical sensor 14.

The first arrangement example is illustrated in FIG. 9A. In the first arrangement example, light in a central portion of the divergent light is incident on the lens 51. The light incident on the lens 51 is not used for detection by the optical sensor 6 or detection by the optical sensor 14. In this case, light in a peripheral portion of the divergent light is used for detection by the optical sensor 6 and detection by the optical sensor 14.

The light in the peripheral portion travels through an annular region located outside the lens 51. Therefore, in the first arrangement example, the optical sensor 6 and the optical sensor 14 are disposed in this annular region.

The second arrangement example is illustrated in FIG. 9B. In the second arrangement example, a parallel flat plate 60 is used. The parallel flat plate 60 is located on the emission side of the lens 51.

In the second arrangement example, most of the divergent light is incident on the lens 51. The divergent light is converted into parallel light by the lens 51. The parallel light emitted from the lens 51 is incident on the parallel flat plate 60. On the parallel flat plate 60, the parallel light is reflected in accordance with the reflectance of the surface. The optical sensor 6 and the optical sensor 14 are disposed in the direction of travel of the reflected parallel light.

In FIG. 9B, the optical sensor 6 is located on the peripheral side of the parallel light, compared with the optical sensor 14. Therefore, light in the peripheral portion of the divergent light is used for detection by the optical sensor 6, and light in the central portion of the divergent light is used for detection by the optical sensor 14.

The third arrangement example is illustrated in FIG. 9C. In the third arrangement example, an optical fiber 61 and an optical fiber 62 are used. Thus, there are fewer restrictions on the position of the optical sensor than in the first arrangement example. For example, it is possible to use fiber bundles as the optical fiber 61 and the optical fiber 62.

In the optical fiber 61, one end surface is located within a light beam of the divergent light, and the other end surface is opposed to the optical sensor 6. In the optical fiber 62, one end surface is located within a light beam of the divergent light, and the other end surface is opposed to the optical sensor 14.

In the third arrangement example, light in a central portion of the divergent light is incident on the lens 51, in the same manner as in the first arrangement example. The light incident on the lens 51 is not used for detection by the optical sensor 6 or detection by the optical sensor 14. In this case, light in a peripheral portion of the divergent light is used for detection by the optical sensor 6 and detection by the optical sensor 14.

The light in the peripheral portion travels through an annular region located outside the lens 51. Therefore, in the third arrangement example, an end surface of the optical fiber 61 and an end surface of the optical fiber 62 are located in the annular region.

In the light source device of the present embodiment, it is preferable that the wavelength selection characteristic of the optical filter be a wavelength selection characteristic in which the wavelength selection characteristic of the wavelength selective filter is shifted to a longer wavelength side, and it is preferable that an amount of the shift be based on an angle between an optical path from the light emitter toward the optical sensor and an optical path from the light emitter toward the optical system.

Figure 10A:
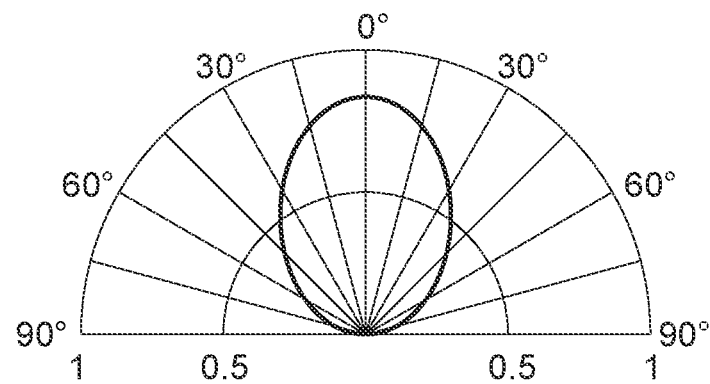
FIGS. 10A and 10B are diagrams illustrating light distribution of a light emitter and an optical sensor arrangement.
Figure 10B:
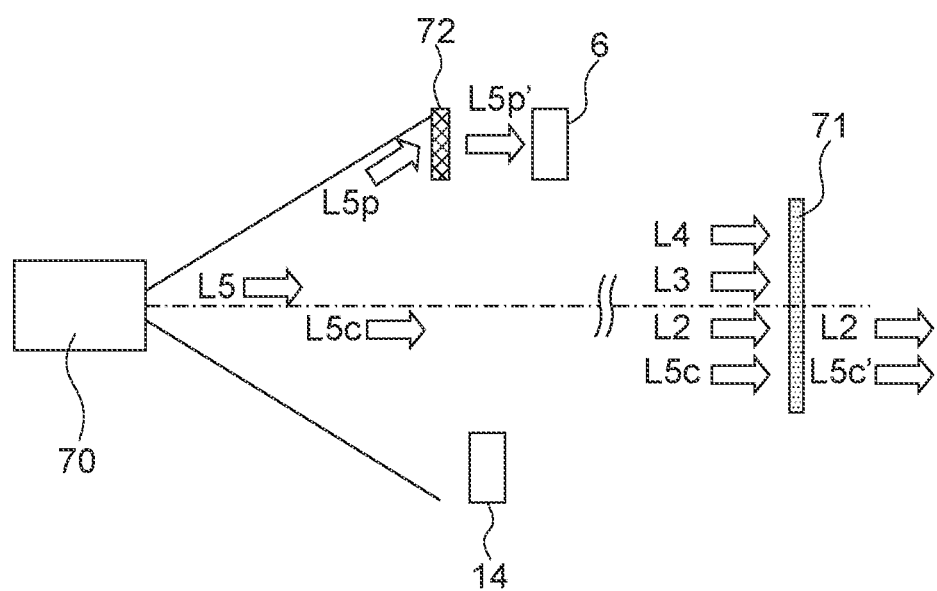

FIGS. 10A and 10B are diagrams illustrating light distribution of a light emitter and an optical sensor arrangement. FIG. 10A is a diagram illustrating light distribution of a light emitter. FIG. 10B is a diagram illustrating a fourth arrangement example. The same component as in FIG. 3A is denoted by the same number and a description thereof will be omitted.

As illustrated in FIG. 10A, light emitted from a light emitter has a spread. The way light spreads is called light distribution, and light distribution is expressed in brightness and angle. The angle represents the angle in the direction in which light travels (hereinafter referred to as "directivity angle"). In the light distribution illustrated in FIG. 10A, brightness decreases as the directivity angle increases.

As illustrated in FIG. 10B, in the fourth arrangement example, a light emitter 70, a wavelength selective filter 71, and an optical filter 72 are used.

The light distribution in the light emitter 70 is the same as the light distribution illustrated in FIG. 10A. Illumination light L5 is emitted from the light emitter 70. Illumination light L5c is light with a small directivity angle of the illumination light L5. The illumination light L5c travels toward the wavelength selective filter 71. Illumination light L5p is light with a large directivity angle of the illumination light L5. The illumination light L5p travels toward the optical filter 72.

The light emitter 70 will be explained in comparison with the light emitter 2. The light distribution in the light emitter 2 is also the same as the light distribution illustrated in FIG. 10A. Therefore, in the illumination light L1 and the illumination light L5, the brightness decreases as the directivity angle increases.

In the light emitter 2, the wavelength band does not shift with the directivity angle. In this case, in the illumination light L1, the wavelength band is the same in light with any directivity angle. Therefore, the wavelength band of light incident on the optical filter 7 is the same as the wavelength band of light incident on the wavelength selective filter 5.

On the other hand, in the light emitter 70, the wavelength band shifts with the directivity angle. In this case, in the illumination light L5, the wavelength band is slightly different in each directivity angle. Therefore, the wavelength band of light incident on the optical filter 72 is different from the wavelength band of light incident on the wavelength selective filter 71.

In the light emitter 70, the illumination light L5c is incident on the wavelength selective filter 71, and the illumination light L5p is incident on the optical filter 72. The wavelength band of the illumination light L5$p$ is different from the wavelength band of the illumination light L5$c$.

Partial band light L5$c'$ is emitted from the wavelength selective filter 71. Detection light L5$p'$ is emitted from the optical filter 72. The detection light L5$p'$ is detected in the optical sensor 6.

Figure 11A:
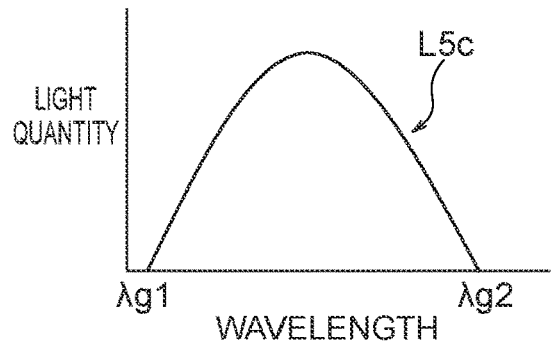
FIGS. 11A, 11B, 11C, 11D, and 11E are diagrams illustrating the wavelength band of illumination light, the characteristic of a wavelength selective filter, and the characteristic of an optical filter.
Figure 11B:
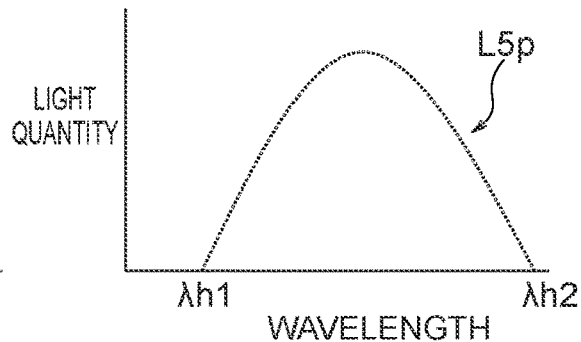
Figure 11C:
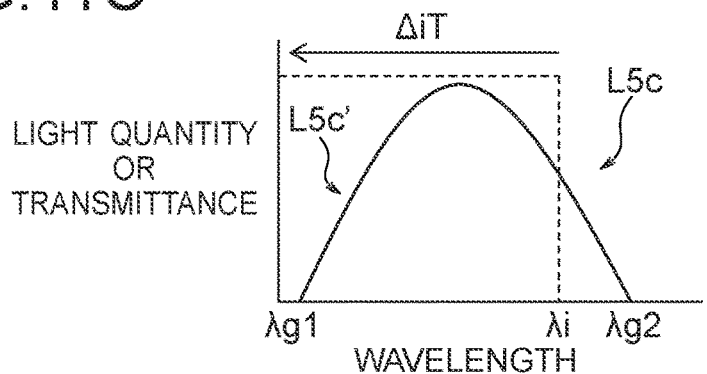
Figure 11D:
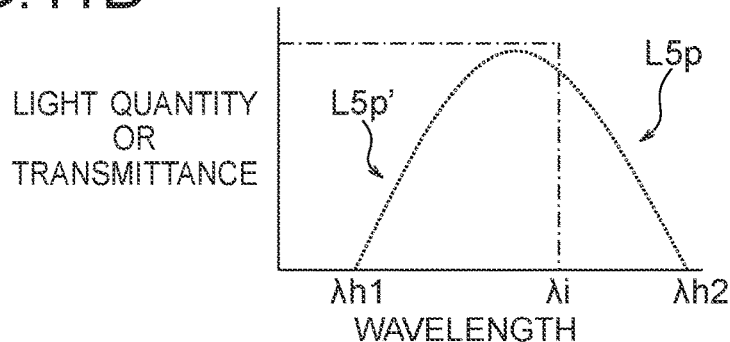
Figure 11E:
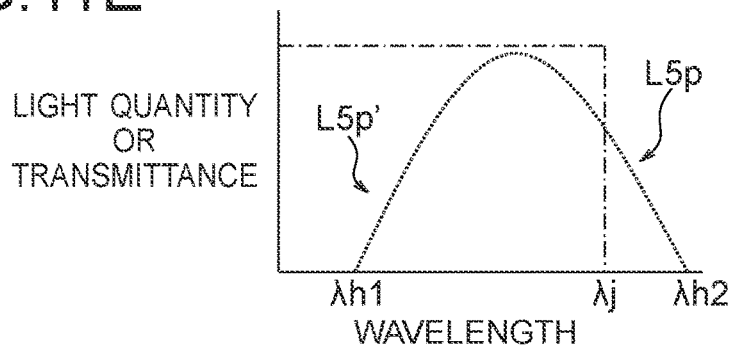

FIGS. 11A, 11B, 11C, 11D, and 11E are diagrams illustrating the wavelength band of illumination light, the characteristic of a wavelength selective filter, and the characteristic of an optical filter. FIG. 11A is a diagram illustrating the wavelength band of light with a small directivity angle. FIG. 11B is a diagram illustrating the wavelength band of light with a large directivity angle. FIG. 11C is a diagram illustrating the wavelength band of light with a small directivity angle and the characteristic of a wavelength selective filter. FIGS. 11D and 11E are diagrams illustrating the wavelength band of light with a large directivity angle and the characteristic of an optical filter.

In FIG. 11A, the wavelength band of the illumination light L5$c$ is depicted. In FIG. 11B, the wavelength band of the illumination light L5$p$ is depicted. The horizontal axis indicates wavelength. The vertical axis indicates light quantity. The light quantity of the illumination light L5$c$ is different from the light quantity of the illumination light L5$p$. In FIGS. 11A and 11B, the light quantity is normalized to 1.

In the light emitter 70, as the directivity angle increases, the wavelength band of the illumination light shifts to the longer wavelength side. Therefore, the wavelength band of the illumination light L5$p$ is located on the longer wavelength side than the wavelength band of the illumination light L5$c$.

The wavelength band of the illumination light L5$c$ is from a wavelength $\lambda$g1 to a wavelength $\lambda$g2. The wavelength band of the illumination light L5$p$ is from a wavelength $\lambda$h1 to a wavelength $\lambda$h2. The wavelength $\lambda$h1 is located on the longer wavelength side than the wavelength $\lambda$g1. The wavelength $\lambda$h2 is located on the longer wavelength side than the wavelength $\lambda$g2.

In FIG. 11C, the wavelength band of the illumination light L5$c$ is depicted by a solid line. Further, the wavelength selection characteristic of the wavelength selective filter 71 is depicted by a broken line. The horizontal axis indicates wavelength. The vertical axis indicates light quantity or transmittance.

As illustrated in FIG. 11C, the wavelength selective filter 71 has a characteristic of transmitting light shorter than a wavelength $\lambda$i. The wavelength band of a transmission band $\Delta$iT is on the shorter wavelength side than the wavelength $\lambda$i. The wavelength band of the partial band light L5$c'$ is included in the transmission band $\Delta$iT. Therefore, as illustrated in FIG. 10B, the partial band light L5$c'$ is emitted from the wavelength selective filter 71.

In the first light emission mode, it is possible to adjust the light quantity in the light emitter 70, based on a signal output from the optical sensor 6. Light detected by the optical sensor 6 is the detection light L5$p'$.

The wavelength band of the detection light L5$p'$ differs depending on the wavelength selection characteristic of the optical filter 72. A case where the optical filter 72 has a first wavelength selection characteristic and a case where the optical filter 72 has a second wavelength selection characteristic will be described.

In FIGS. 11D and 11E, the wavelength band of the illumination light L5$p$ is depicted by a dotted line. Further, in FIG. 11D, the first wavelength selection characteristic is depicted by an alternate long and short dash line. In FIG. 11E, the second wavelength selection characteristic is depicted by an alternate long and short dash line. The horizontal axis indicates wavelength. The vertical axis indicates light quantity or transmittance.

The first wavelength selection characteristic is the same as the wavelength selection characteristic of the wavelength selective filter 71. As illustrated in FIG. 11D, the transmission band is on the shorter wavelength side than the wavelength $\lambda$i. The wavelength band of the detection light L5$p'$ is from the wavelength $\lambda$h1 to the wavelength $\lambda$i.

The second wavelength selection characteristic is different from the wavelength selection characteristic of the wavelength selective filter 71. The second wavelength selection characteristic is a wavelength selection characteristic in which the wavelength selection characteristic of the wavelength selective filter 71 is shifted to the longer wavelength side. As illustrated in FIG. 11E, the transmission band is on the shorter wavelength side than a wavelength $\lambda$j. The wavelength band of the detection light L5$p'$ is from the wavelength $\lambda$h1 to the wavelength $\lambda$j. The wavelength $\lambda$j is located on the longer wavelength side than the wavelength $\lambda$i.

When FIGS. 11D and 11E are compared, the area demarcated by the characteristic curve is different between the transmission band of the first wavelength selection characteristic and the transmission band of the second wavelength selection characteristic. The transmission band of the second wavelength selection characteristic is wider than the wavelength band of the first wavelength selection characteristic. Therefore, the area in the second wavelength selection characteristic is larger than the area in the first wavelength selection characteristic.

The difference between the area demarcated by the wavelength selection characteristic of the wavelength selective filter 71 and the area in the first wavelength selection characteristic is defined as a first difference. The difference between the area demarcated by the wavelength selection characteristic of the wavelength selective filter 71 and the area in the second wavelength selection characteristic is defined as a second difference. As described above, the area in the second wavelength selection characteristic is larger than the area in the first wavelength selection characteristic is. Therefore, the second difference is smaller than the first difference.

In this way, in the second wavelength selection characteristic, an area similar to the area demarcated by the wavelength selection characteristic of the wavelength selective filter 71 can be obtained. Therefore, by imparting the second wavelength selection characteristic to the optical filter 72, it is possible to adjust the light quantity in the light emitter 2 with high accuracy. As a result, illumination light even more suitable for observation can be obtained in the first light emission mode.

The second wavelength selection characteristic of the optical filter 72 is the wavelength selection characteristic when the wavelength selection characteristic of the wavelength selective filter 71 is shifted to the longer wavelength side. The amount of shift is based on the angle between an optical path in a first direction and an optical path in a second direction.

The optical path in the first direction is an optical path from the light emitter 70 toward the optical sensor 6. The optical path in the second direction is an optical path from the light emitter 70 toward the wavelength selective filter 71. As illustrated in FIG. 3A, the optical system 13 is disposed on the optical path toward the wavelength selective filter 5. The optical system 13 is also disposed on the optical path from the light emitter 70 toward the wavelength selective filter 71. Therefore, the optical path in the second direction may be defined as the optical path from the light emitter toward the optical system.

The amount of shift of the second wavelength selection characteristic relative to the first wavelength selection characteristic is expressed as the difference between the wavelength $\lambda j$ and the wavelength $\lambda i$. The amount of shift of the wavelength band of the illumination light L5$p$ relative to the wavelength band of the illumination light L5$c$ is expressed as the difference between the wavelength $\lambda h1$ and a wavelength $\lambda g1$. The difference between the wavelength $\lambda j$ and the wavelength $\lambda i$ is smaller than the difference between the wavelength $\lambda h1$ and the wavelength $\lambda g1$. Therefore, in the optical filter 72, the amount of shift of the wavelength selection characteristic relative to the wavelength selection characteristic of the wavelength selective filter 5 is different from the amount of shift of the wavelength band in the illumination light.

Figure 12A:
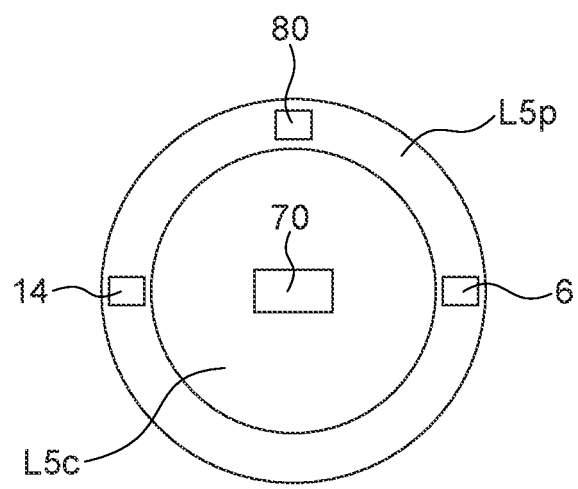
FIGS. 12A and 12B are diagrams illustrating an optical sensor arrangement.
Figure 12B:
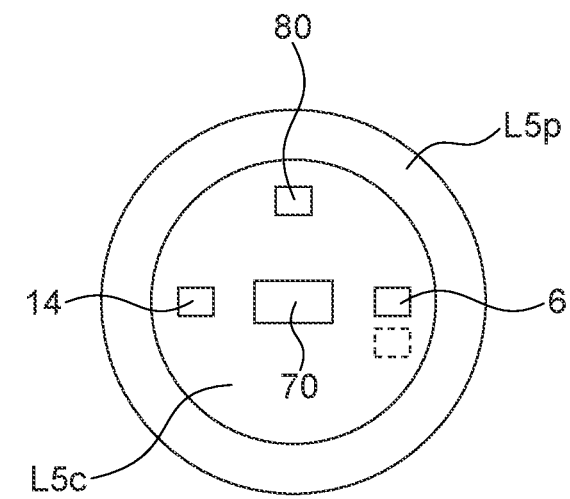

FIGS. 12A and 12B are diagrams illustrating an optical sensor arrangement. FIG. 12A is a diagram illustrating a fifth arrangement example. FIG. 12B is a diagram illustrating a sixth arrangement example. The same component as in FIG. 10B is denoted by the same number and a description thereof will be omitted.

As described above, in the light emitter 70, the wavelength band shifts with the directivity angle. Therefore, the wavelength band of the illumination light L5$c$ is different from the wavelength band of the illumination light L5$p$. When a plurality of optical sensors are used, it is preferable to dispose each optical sensor in a region where light of the same wavelength band reaches.

The fifth arrangement example is illustrated in FIG. 12A. FIG. 12A illustrates a state in which the light emitter 2 is viewed from the lens 51 side in the first arrangement example (FIG. 9A). However, the light emitter 2 is replaced by the light emitter 70.

In the fifth arrangement example, the illumination light L5$c$ is incident on the lens 51. In this case, it is impossible to dispose the optical sensor 6 and the optical sensor 14 within the region of the illumination light L5$c$. Therefore, the optical sensor 6 and the optical sensor 14 must be disposed within the region of the illumination light L5$p$.

Within the region of the illumination light L5$p$, the wavelength band is substantially the same, regardless of position. In the fifth arrangement example, consequently, the optical sensor 6 and the optical sensor 14 are disposed in substantially the same wavelength band.

The number of optical sensors disposed within the region of the illumination light L5$p$ is not limited. Furthermore, it is possible to dispose an optical sensor 80. It is possible to use the optical sensor 80 together with an optical filter (not illustrated). The wavelength selection characteristic of the optical filter is different from the optical property of the optical filter 6 and the optical property of the optical filter 72.

Since the shape of the region of the illumination light L5$p$ is annular and the annular width is narrow, the distance from the center to the optical sensor is the same or substantially the same, no matter where the optical sensor is disposed.

In the fifth arrangement example, the optical sensor 6, the optical sensor 14, and the optical sensor 80 receive light from the light emitter 70. Therefore, the light source device includes a plurality of optical sensors that receive light from one light emitter. The center of the light-emitting surface of the light emitter 70 is defined as center C (not illustrated), the direction from the center C toward the optical sensor 6 is defined as a first direction, the direction from the center C toward the optical sensor 14 is defined as a second direction, and the direction from the center C toward the optical sensor 80 is defined as a third direction. In a fifth arrangement example, the first direction, the second direction, and the third direction are different from each other. When the normal at the center C is the optical axis of the light emitter 70, the angle between the optical axis and the first direction, the angle between the optical axis and the second direction, and the angle between the optical axis and the third direction are the same. Therefore, a plurality of sensors are installed in an identical tilt angle direction relative to the optical axis of the light emitter.

The sixth arrangement example is illustrated in FIG. 12B. FIG. 12B illustrates a state in which the parallel flat plate 60 is viewed from the optical sensor 6 side in the second arrangement example (FIG. 9B). However, the light emitter 2 is replaced by the light emitter 70.

In the sixth arrangement example, the illumination light L5$c$ and the illumination light L5$p$ are emitted from the lens 51. In this case, it is possible to dispose the optical sensor 6, the optical sensor 14, and the optical sensor 80 within a region in which the region of the illumination light L5$c$ and the region of the illumination light L5$p$ are combined.

In the sixth arrangement example, the optical sensor 6, the optical sensor 14, and the optical sensor 80 are disposed within the region of the illumination light L5$c$. However, these optical sensors may be disposed within the region of the illumination light L5$p$, in the same manner as in the fifth arrangement example.

In FIG. 12B, the boundary between the illumination light L5$c$ and the illumination light L5$p$ is illustrated for comparison with the fifth arrangement example. However, in the sixth arrangement example, the boundary between the illumination light L5$c$ and the illumination light L5$p$ actually does not exist. Therefore, the optical sensor 6, the optical sensor 14, and the optical sensor 80 may be disposed at the boundary between the illumination light L5$c$ and the illumination light L5$p$.

Within the region of the illumination light L5$c$, the wavelength band differs depending on the position. Therefore, within the region of the illumination light L5$c$, each optical sensor is disposed such that the distance from the center to the optical sensor is the same. As a result, the optical sensor 6, the optical sensor 14, and the optical sensor 80 are disposed in substantially the same wavelength band.

When the wavelength band does not shift with the directivity angle, it is possible to dispose the optical sensor 14 at the position indicated by a broken line.

An endoscope system of the present embodiment includes an endoscope, a video processor, a monitor, and the light source device described above.

Figure 13:
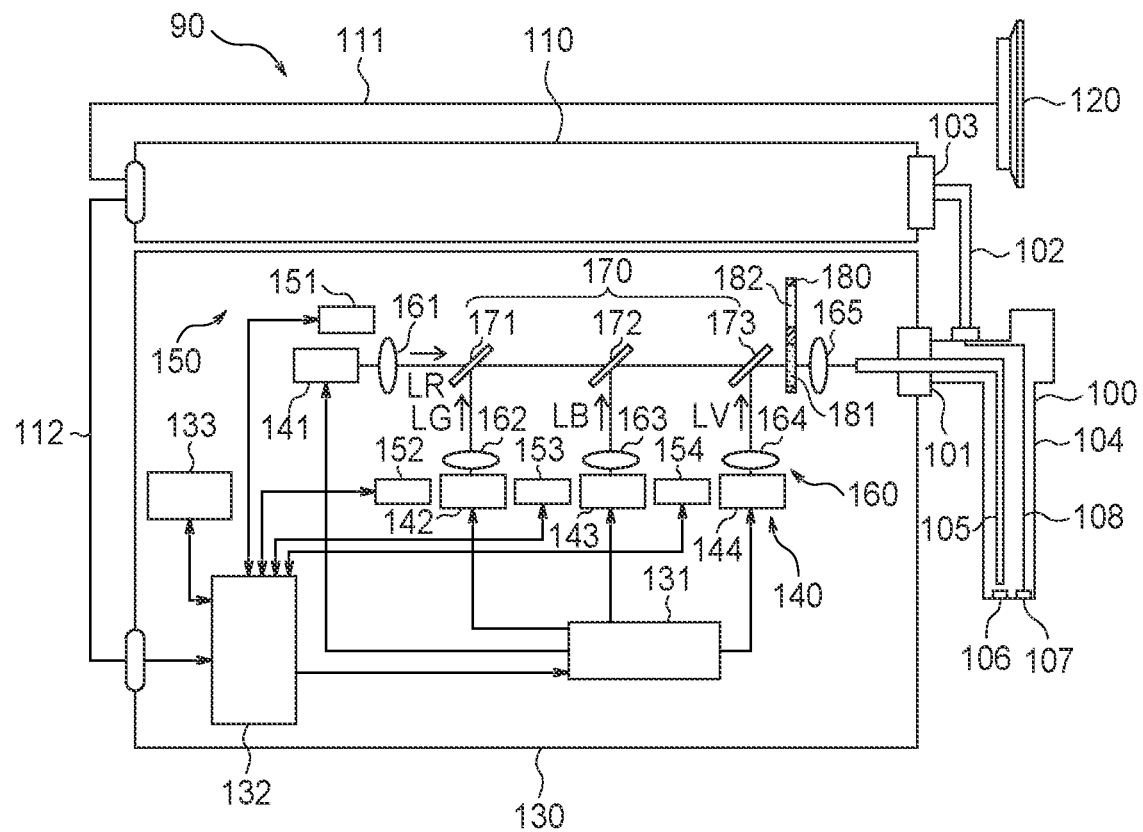
FIG. 13 is a diagram illustrating an endoscope system of the present embodiment.

FIG. 13 is a diagram illustrating an endoscope system of the present embodiment. An endoscope system 90 includes an endoscope 100, a video processor 110, a monitor 120, and a light source device 130.

The endoscope 100 is connected to the light source device 130 through a connector 101 and connected to the video processor 110 through a cable 102 and a connector 103.

The endoscope 100 has an insertion section 104. The insertion section 104 contains a light guide 105, a lens 106, an image pickup unit 107, and a signal line 108.

The light guide 105 guides illumination light generated by the light source device 130 to the lens 106. Illumination light is emitted from the lens 106.

The image pickup unit 107 includes an objective optical system and an image pickup element. A drive signal is transmitted to the image pickup element from the video processor 110 through the signal line 108. The image pickup element generates an image signal from an optical image formed by the objective optical system. The image signal is output to the video processor 110 through the signal line 108.

The image signal is processed if necessary in the video processor 110. The image signal is output to the monitor 120 through a cable 111. An endoscopic image is displayed on the monitor 120, based on the image signal.

The video processor 110 can control the light source device 130 such that the brightness of the endoscopic image attains target brightness. Information to control the light source device 130 is supplied to the light source device 130 through a cable 112.

The light source device 130 includes a plurality of light emitters 140, a plurality of optical sensors 150, a plurality of lenses 160, a combining optical system 170, a drive unit 131, a control unit 132, and a memory 133.

The light emitters 140 include a light emitter 141, a light emitter 142, a light emitter 143, and a light emitter 144.

Illumination light LR is emitted from the light emitter 141. The illumination light LR is red light. Illumination light LG is emitted from the light emitter 142. The illumination light LG is green light. Illumination light LB is emitted from the light emitter 143. The illumination light LB is blue light. Illumination light LV is emitted from the light emitter 144. The illumination light LV is violet light.

The optical sensors 150 include an optical sensor 151, an optical sensor 152, an optical sensor 153, and an optical sensor 154.

The optical sensor 151 is disposed at a position where the illumination light LR reaches. The optical sensor 152 is disposed at a position where the illumination light LG reaches. The optical sensor 153 is disposed at a position where the illumination light LB reaches. The optical sensor 154 is disposed at a position where the illumination light LV reaches.

The lenses 160 include a lens 161, a lens 162, a lens 163, a lens 164, and a lens 165.

The illumination light LR is incident on the lens 161. The lens 161 converts the illumination light LR into parallel light. The illumination light LG is incident on the lens 162. The lens 162 converts the illumination light LG into parallel light. The illumination light LB is incident on the lens 163. The lens 163 converts the illumination light LB into parallel light. The illumination light LV is incident on the lens 164. The lens 164 converts the illumination light LV into parallel light.

The illumination light LR, the illumination light LG, the illumination light LB, and the illumination light LV are incident on the combining optical system 170. The combining optical system 170 includes a dichroic mirror 171, a dichroic mirror 172, and a dichroic mirror 173.

The illumination light LR and the illumination light LG are incident on the dichroic mirror 171. The illumination light LR and the illumination light LG are combined by the dichroic mirror 171. The illumination light LB is incident on the dichroic mirror 172. The illumination light LR, the illumination light LG, and the illumination light LB are combined by the dichroic mirror 172. The illumination light LV is incident on the dichroic mirror 173. The illumination light LR, the illumination light LG, the illumination light LB, and the illumination light LV are combined by the dichroic mirror 173.

The illumination light LR, the illumination light LG, the illumination light LB, and the illumination light LV reach the rotating member 180. The rotating member 180 includes a wavelength selective filter 181 and a parallel flat plate 182.

When the wavelength selective filter 181 is located on the optical path, the illumination light LB and partial band light LV' are emitted from the wavelength selective filter 181 (the partial band LV' is not illustrated). In this case, illumination light in the first light emission mode, that is, illumination light suitable for narrow-band light observation, can be obtained.

When the parallel flat plate 182 is located on the optical path, the illumination light LR, the illumination light LG, the illumination light LB, and the illumination light LV are emitted from the parallel flat plate 181. In this case, illumination light in the second light emission mode, that is, illumination light suitable for normal observation, can be obtained.

The light emitted from the wavelength selective filter 181 or the light emitted from the parallel flat plate 182 is collected by the lens 165. An end surface of the light guide 105 is located at the light collected position. The collected light is incident on the light guide 105 and is guided to the lens 106. An object is illuminated by the light emitted from the lens 106.

In the light emitters 140, each of the light emitters is connected to the drive unit 131. In the drive unit 131, the light emitter is turned on and off. As a result, it is possible to perform PWM control. The light quantity in the light emitter is adjusted by performing PWM control. Information on the adjustment is stored in the memory 133.

In the endoscope system 90, the information on the adjustment is used to adjust the light quantity in each light emitter. Thus, when the light quantity in each light emitter changes, it is possible to maintain the ideal color balance by performing adjustment. As a result, illumination light suitable for observation can be obtained in the first light emission mode and the second light emission mode.

As described above, the present disclosure is suitable for a light source device that can maintain ideal color balance even when the light quantity in the light emitter changes, and for an endoscope system that can acquire a clear image.

According to the present disclosure, it is possible to provide a light source device that can maintain ideal color balance even when the light quantity in the light emitter changes, and an endoscope system that can acquire a clear image.

What is claimed is:

1. A light source device comprising:
    a plurality of light emitters;
    an optical system configured to combine light from the light emitters;
    a wavelength selective filter located on an optical path of the optical system; and
    an optical sensor configured to receive light from one light emitter among the light emitters through an optical filter, wherein
    the optical filter has a wavelength selection characteristic corresponding to a wavelength selection characteristic of the wavelength selective filter.

2. The light source device according to claim 1, wherein the wavelength selection characteristic of the optical filter is identical to the wavelength selection characteristic of the wavelength selective filter.

3. The light source device according to claim 1, wherein the light source device has a plurality of light emission modes, in the light emission modes, a wavelength band of emitted light is different in each of the light emission modes, and the light emission modes include a first light emission mode in which the wavelength selective filter is located on the optical path and a second light emission mode in which the wavelength selective filter is not located on the optical path.

4. The light source device according to claim 3, wherein the light source device comprises a plurality of optical sensors, one of the plurality of optical sensors is the optical sensor, the plurality of optical sensors receive light from the one light emitter, and in the optical sensors, wavelength bands of received light are different from each other.

5. The light source device according to claim 3, wherein the light source device comprises a plurality of optical filters, one of the plurality of optical filters is the optical filter, in the plurality of optical filters, wavelength selection characteristics are different from each other, and the optical filters are switched and light is received by the optical sensor.

6. The light source device according to claim 1, wherein the wavelength selection characteristic of the optical filter is a wavelength selection characteristic in which the wavelength selection characteristic of the wavelength selective filter is shifted to a longer wavelength side, and an amount of the shift is based on an angle between an optical path from the light emitter toward the optical sensor and an optical path from the light emitter toward the optical system.

7. The light source device according to claim 3, wherein the light source device comprises a plurality of optical sensors configured to receive light from the one light emitter, and the plurality of optical sensors are installed in an identical tilt angle direction relative to an optical axis of the light emitter.

8. An endoscope system comprising:

an endoscope;

a video processor;

a monitor; and the light source device according to claim 1.

* * * * *